(12) United States Patent
Soni

(10) Patent No.: US 12,150,695 B2
(45) Date of Patent: *Nov. 26, 2024

(54) SURGICAL INSTRUMENT WITH INCREASED LEVER STROKE

(71) Applicant: Covidien LP, Mansfield, MA (US)

(72) Inventor: Purvishkumar H. Soni, Longmont, CO (US)

(73) Assignee: Covidien LP, Mansfield, MA (US)

( * ) Notice: Subject to any disclaimer, the term of this patent is extended or adjusted under 35 U.S.C. 154(b) by 551 days.

This patent is subject to a terminal disclaimer.

(21) Appl. No.: 17/496,882

(22) Filed: Oct. 8, 2021

(65) Prior Publication Data
US 2022/0022944 A1  Jan. 27, 2022

Related U.S. Application Data

(63) Continuation of application No. 16/354,524, filed on Mar. 15, 2019, now Pat. No. 11,147,613.

(51) Int. Cl.
*A61B 18/12* (2006.01)
*A61B 17/28* (2006.01)
(Continued)

(52) U.S. Cl.
CPC ........ *A61B 18/1445* (2013.01); *A61B 17/282* (2013.01); *A61B 17/2909* (2013.01);
(Continued)

(58) Field of Classification Search
CPC .............. A61B 18/1445; A61B 18/085; A61B 18/1482; A61B 18/1206; A61B 2018/1412; A61B 2018/1455
See application file for complete search history.

(56) References Cited

U.S. PATENT DOCUMENTS

D249,549 S   9/1978 Pike
D263,020 S   2/1982 Rau, III
(Continued)

FOREIGN PATENT DOCUMENTS

CN   201299462 Y   9/2009
DE   2415263 A1    10/1975
(Continued)

OTHER PUBLICATIONS

Michael Choti, "Abdominoperineal Resection with the LigaSure Vessel Sealing System and Lig5b4aSure Atlas 20 cm Open Instrument"; Innovations That Work, Jun. 2003.
(Continued)

*Primary Examiner* — Daniel W Fowler

(57) ABSTRACT

A surgical instrument includes a housing having an elongated shaft extending distally therefrom configured to support an end effector at a distal end thereof. A handle operably couples to a drive assembly and is moveable to actuate the end effector. The drive assembly includes: front and rear drive tubes, the rear drive tube including a front washer disposed at a distal end thereof, the front drive tube including a rear washer disposed at a proximal end thereof; a stopper slidably disposed atop the front tube, the stopper and the rear washer defining a dead space therebetween; and a spring operably associated with the stopper. Initial actuation of the handle moves the front and rear drive tubes to close the end effector to grasp tissue and, once closed, further movement of the handle moves the rear drive tube to slide the stopper to eliminate the dead space.

20 Claims, 28 Drawing Sheets

(51) Int. Cl.
  *A61B 17/29* (2006.01)
  *A61B 18/08* (2006.01)
  *A61B 18/14* (2006.01)
  *A61B 18/00* (2006.01)

(52) U.S. Cl.
  CPC ........ *A61B 18/085* (2013.01); *A61B 18/1206* (2013.01); *A61B 18/1482* (2013.01); *A61B 2017/2913* (2013.01); *A61B 2017/2946* (2013.01); *A61B 2018/00083* (2013.01); *A61B 2018/00589* (2013.01); *A61B 2018/00595* (2013.01); *A61B 2018/00601* (2013.01); *A61B 2018/00619* (2013.01); *A61B 2018/0063* (2013.01); *A61B 2018/00916* (2013.01); *A61B 2018/1412* (2013.01); *A61B 2018/1455* (2013.01)

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| 5,897,564 A * | 4/1999 | Schulze ............ A61B 17/0483 112/80.03 |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bor |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| 7,255,697 B2 | 8/2007 | Dycus et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 9,084,608 B2 | 7/2015 | Larson et al. |
| 9,211,657 B2 | 12/2015 | Ackley et al. |
| 11,147,613 B2 | 10/2021 | Soni |
| 2007/0282332 A1 | 12/2007 | Witt et al. |
| 2012/0296333 A1 | 11/2012 | Twomey |
| 2013/0030428 A1 | 1/2013 | Worrell et al. |
| 2014/0076955 A1 * | 3/2014 | Lorenz ............ A61B 17/07207 227/176.1 |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276738 A1 | 9/2014 | Price et al. |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |

FOREIGN PATENT DOCUMENTS

| | | | |
|---|---|---|---|
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |

(56) References Cited

FOREIGN PATENT DOCUMENTS

| | | |
|---|---|---|
| DE | 102008018406 B3 | 7/2009 |
| EP | 1159926 A2 | 12/2001 |
| EP | 1281878 A1 | 2/2003 |
| JP | 61501068 | 9/1984 |
| JP | 6502328 | 3/1992 |
| JP | 55106 | 1/1993 |
| JP | H0540112 A | 2/1993 |
| JP | 6121797 | 5/1994 |
| JP | 6285078 | 10/1994 |
| JP | H06343644 A | 12/1994 |
| JP | H07265328 A | 10/1995 |
| JP | 08056955 | 3/1996 |
| JP | 08252263 | 10/1996 |
| JP | 8289895 | 11/1996 |
| JP | 8317934 | 12/1996 |
| JP | 8317936 | 12/1996 |
| JP | 09000538 | 1/1997 |
| JP | H0910223 A | 1/1997 |
| JP | 9122138 | 5/1997 |
| JP | 1024051 | 1/1998 |
| JP | 0010000195 | 1/1998 |
| JP | 10155798 | 6/1998 |
| JP | 1147149 | 2/1999 |
| JP | 1147150 | 2/1999 |
| JP | 11070124 | 3/1999 |
| JP | 11169381 | 6/1999 |
| JP | 11192238 | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 | 1/2001 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| JP | 6511401 | 5/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A3 | 4/2006 |
| WO | 2008040483 A1 | 4/2008 |
| WO | 2011018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. Jan. 1, 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas MedicalCenter, Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000, 6 bages.
Johnson et al. "Evaluation of a Bipolar Electrothermal Vessel Sealing Device in Hemorrhoidectomy" Sales/Product Literature; Jan. 2004, 1 page.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidecto 144rmy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Su5b4rgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Me5b4chanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 39, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/ Product Literature 2001, 1 page.
Bergdahl et al. "Studies on Coagulation and the Development of an Automatic Computerized Bipolar Coagulator" J. Neu5b4rosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

(56) References Cited

OTHER PUBLICATIONS

Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003. (15 pages.).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 15b4 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; NCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler (abandoned).
U.S. Appl. No. 09/177,950, filed O5b4ct. 23, 1998; inventor: Randel A. Frazier, abandoned.
U.S. Appl. No. 09/387,883; filed Sep. 1, 1999; inventor: Dale F. Schmaltz (abandoned).
U.S. Appl. No. 09/591,328, filed Jun. 9, 2000; inventor: Thomas P. Ryan (abandoned).
U.S. Appl. No. 12/336,970; filed Dec. 17, 2008; inventor: Paul R. Sremeich (abandoned).
U.S. Appl. No. 14/065,644, filed Oct. 29, 2013; inventor: Reschke (abandoned).
Heniford et al. "Initial Research and Clinical Results with an Electrothermal Bipolar Vessel Sealer" Oct. 1999.

\* cited by examiner

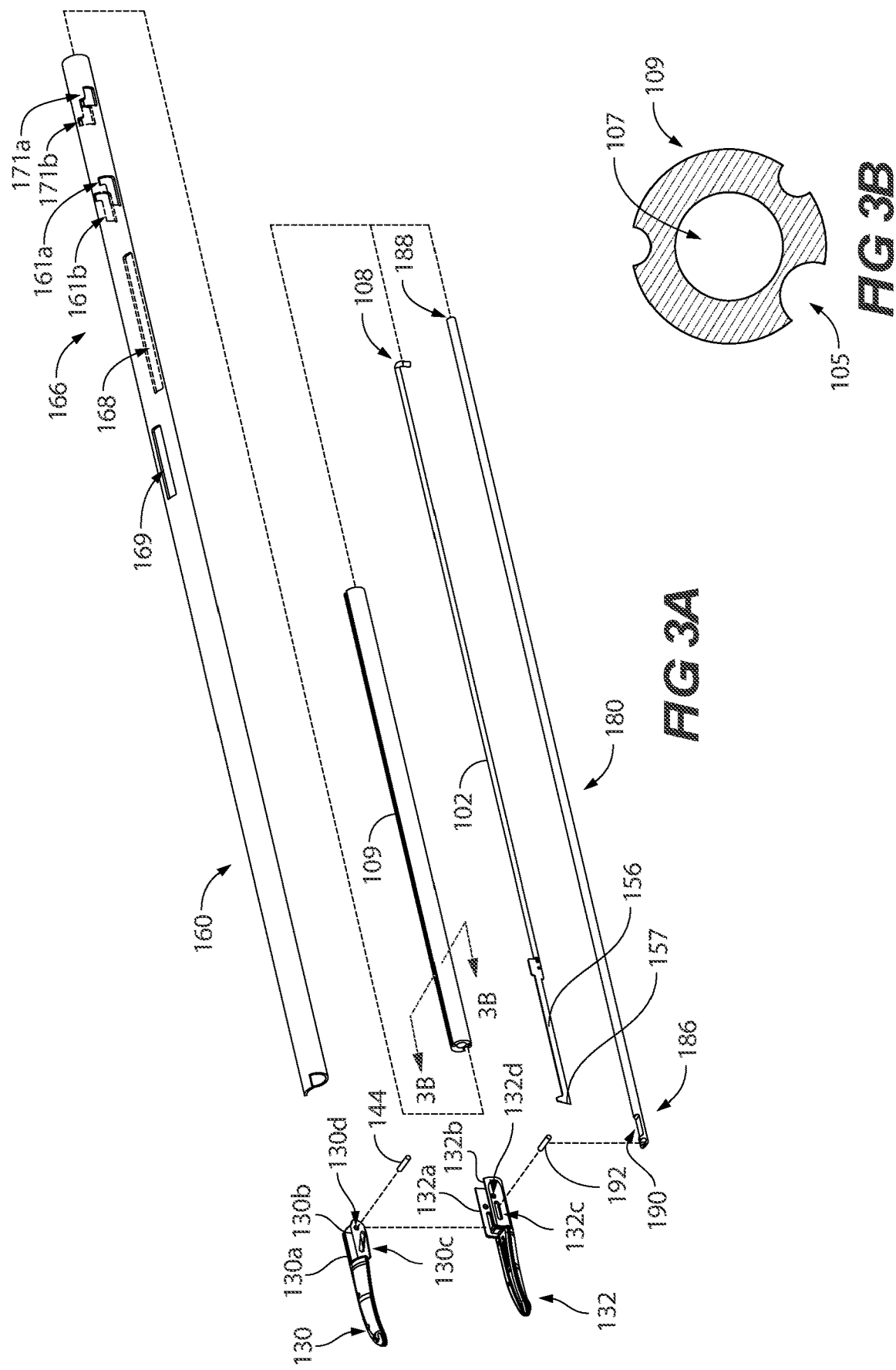

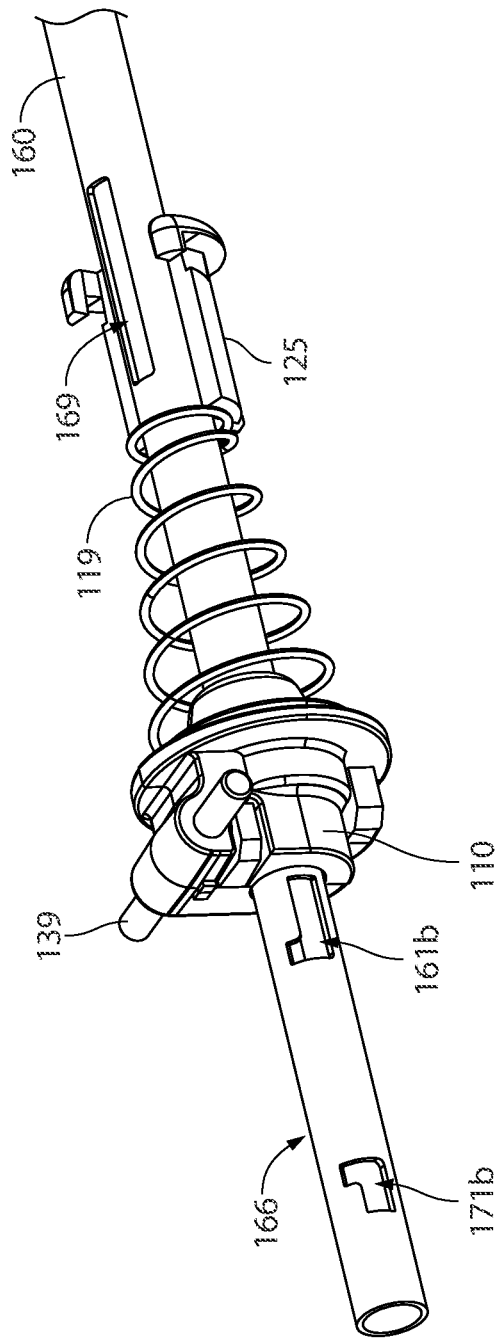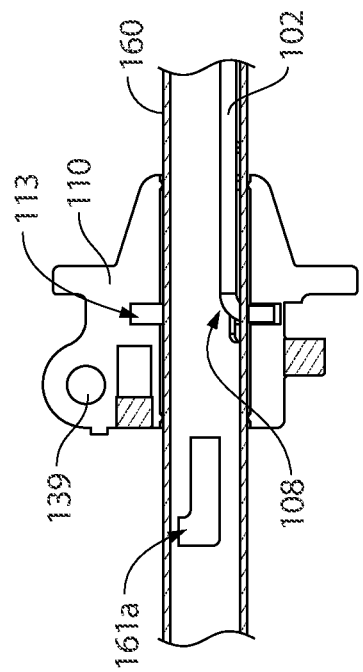

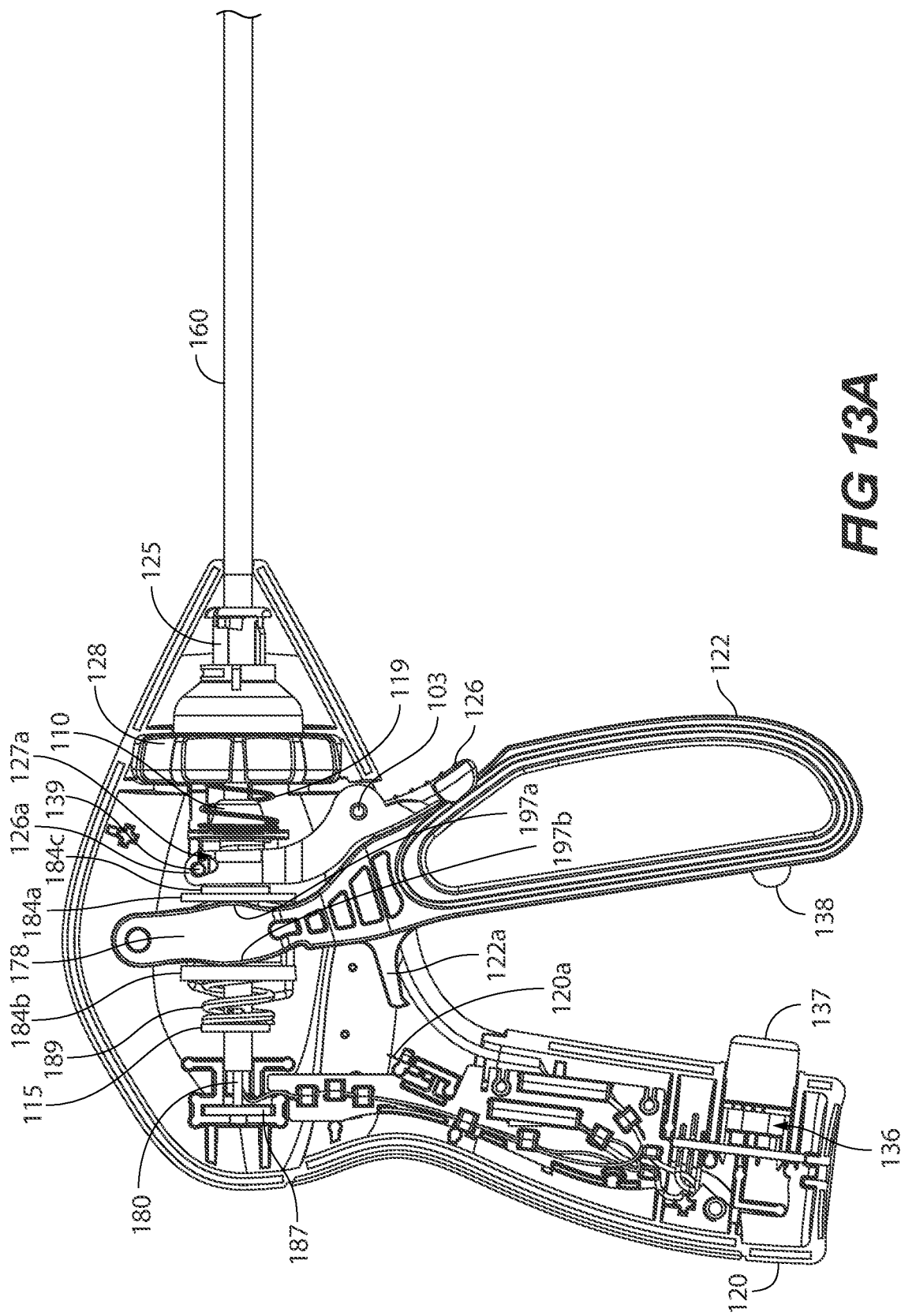

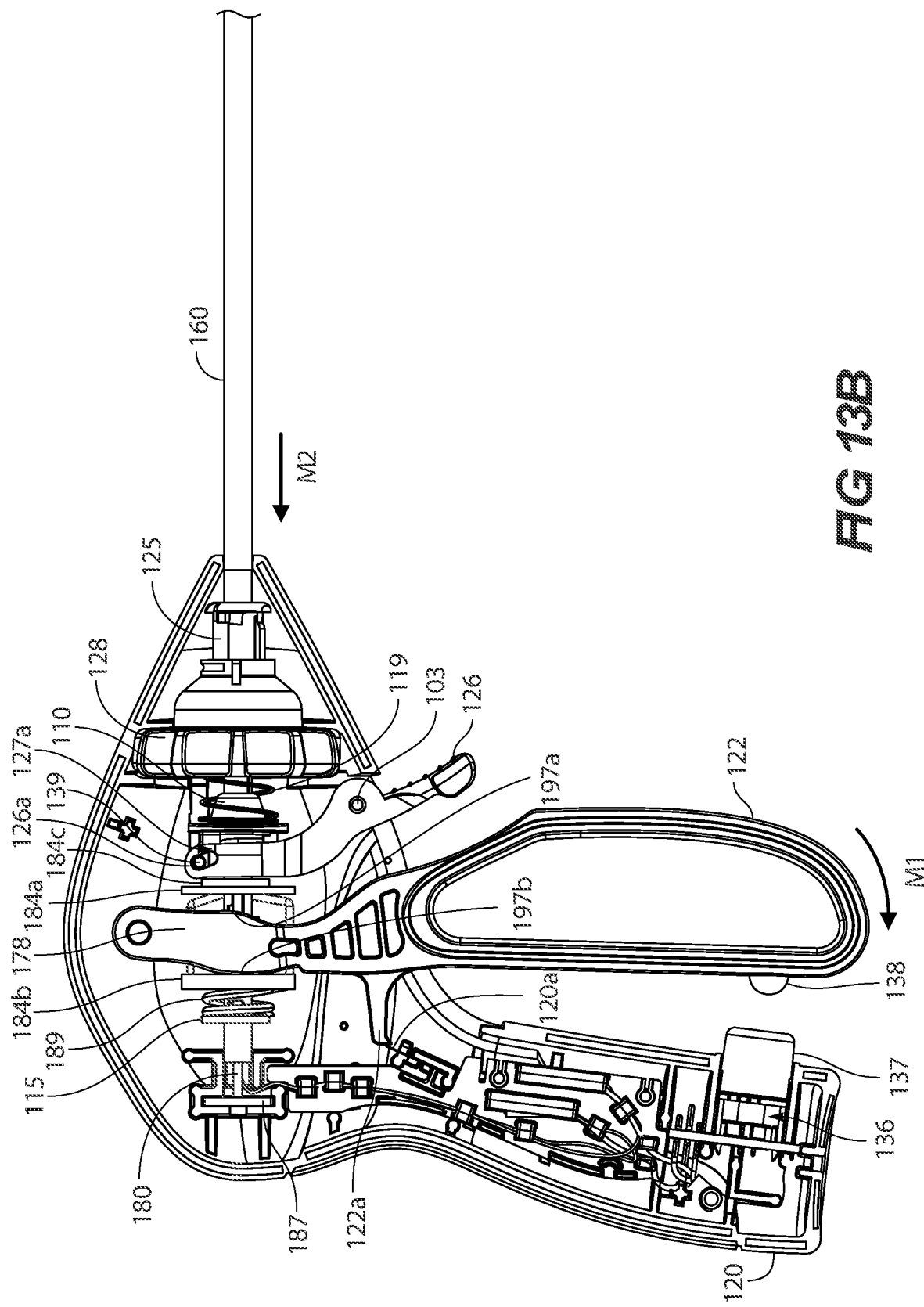

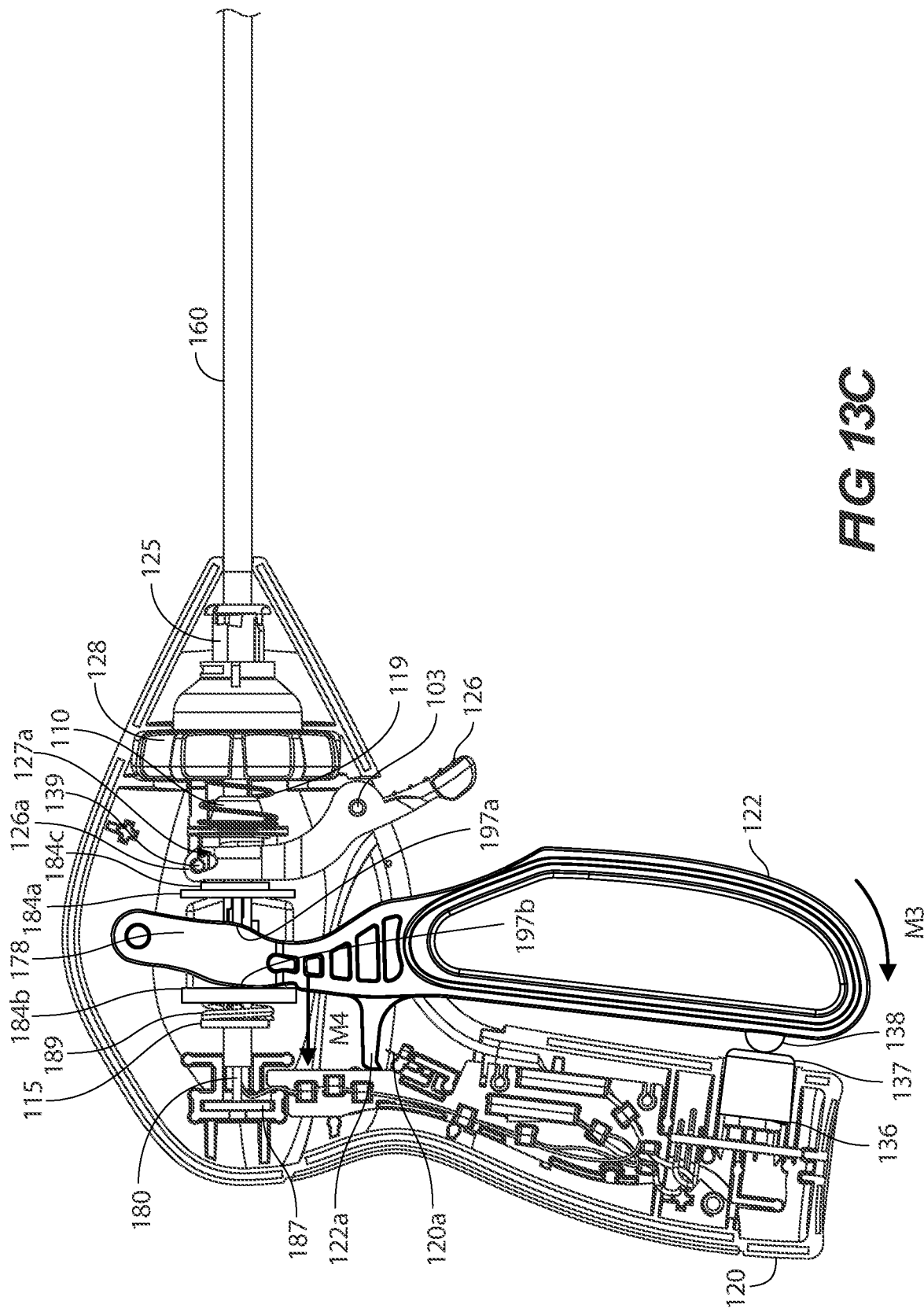

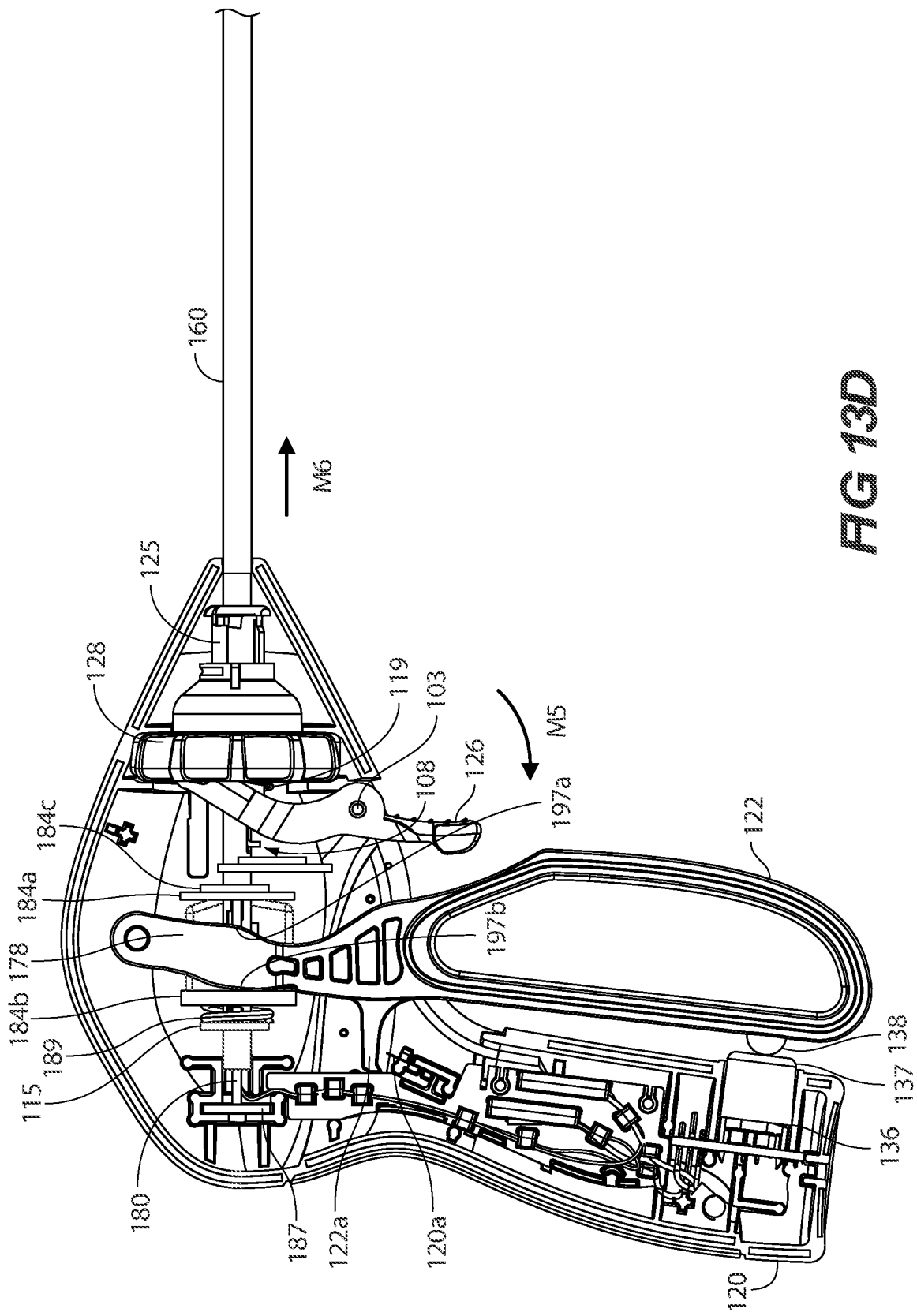

SURGICAL INSTRUMENT WITH INCREASED LEVER STROKE

The present application is a continuation application of U.S. application Ser. No. 16/354,524 filed on Mar. 15, 2019, the entire contents of which are incorporated herein by reference.

BACKGROUND

1. Technical Field

The present disclosure relates generally to the field of surgical instruments. In particular, the disclosure relates to an endoscopic electrosurgical forceps that is economical to manufacture and is capable of sealing and cutting relatively large tissue structures.

2. Background of Related Art

Instruments such as electrosurgical forceps are commonly used in open and endoscopic surgical procedures to coagulate, cauterize and seal tissue. Such forceps typically include a pair of jaw members that can be controlled by a surgeon to grasp targeted tissue, such as, e.g., a blood vessel. The jaw members may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaw members. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaw members. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 $kg/cm^2$ to about 16 $kg/cm^2$.

Many endoscopic surgical instruments utilize handle or levers to actuate the end effector assembly typically disposed at a distal end of the instrument. For example, actuation of the handle correspondingly actuates the jaw members in an endoscopic forceps typically with a one-to-one (1:1) ratio. Once closed about tissue the surgeon activates the electrical energy to treat tissue. With endoscopic instruments with in-line activation surgeons' prefer a clear distinction between full closure of the jaw members and in-line activation. Audible tones and various haptic interfaces are common feedback devices utilized for this purpose.

SUMMARY

As used herein, the term "distal" refers to the portion of the instrument or component thereof that is being described that is further from a user, while the term "proximal" refers to the portion of the instrument or component thereof that is being described that is closer to a user. Further, to the extent consistent, any of the aspects described herein may be used in conjunction with any of the other aspects described herein. As used herein the term "tissue" is meant to include variously-sized vessels.

Provided in accordance with aspects of the present disclosure is a surgical instrument including a housing having an elongated shaft extending distally from the housing and configured to support an end effector assembly at a distal end thereof, the end effector assembly including first and second jaw members. A handle is operably coupled to a drive assembly and is moveable relative to the housing to actuate the end effector assembly and move one or both of the jaw members relative to the other of the jaw members to grasp tissue therebetween. The drive assembly includes: a rear drive tube and a front drive tube, the rear drive tube including a front washer disposed at a distal end thereof, the front drive tube including a rear washer disposed at a proximal end thereof; a spring collar disposed atop the rear drive tube between a drive spring washer and a rear stop; a stopper tube slidably disposed atop the front tube between the front washer and the rear washer, the stopper tube and the rear washer defining a dead space therebetween; a jaw force spring operably associated with the spring collar and biased between the drive spring washer and the rear stop; and a spring operably associated with the stopper tube and biased between the front and rear washers.

Initial actuation of the handle relative to the housing moves the front and rear drive tubes to move the jaw members to the closed position to grasp tissue and, once closed, further movement of the handle in the same direction moves the rear drive tube relative to the front drive tube to move the front washer and slide the stopper tube towards the rear washer to eliminate the dead space therebetween.

In aspects according to the present disclosure, the handle is configured to move proximally from a distal-most position towards the housing to move the first and second jaw members. In other aspects according to the present disclosure, initial movement of the handle moves the front and rear drive tubes proximally. In still other aspects according to the present disclosure, further movement of the handle beyond the initial movement of the handle moves the front washer proximally and slides the stopper tube towards the rear washer to eliminate the dead space therebetween.

In aspects according to the present disclosure, after movement of the handle to eliminate the dead space, further movement of the handle towards the housing compresses the jaw force spring and moves the spring collar atop the rear drive tube to provide a closure force between the first and second jaw members. In aspects, the closure force may be within a range of about 3 $kg/cm^2$ to about 15 $kg/cm^2$.

In aspects according to the present disclosure, after movement of the handle compresses the jaw force spring to provide the closure force to the first and second jaw members, further movement of the handle towards the housing activates a switch disposed in the housing to provide electrosurgical energy to the jaw members to seal tissue disposed therebetween. In other aspects according to the present disclosure, the switch is operably associated with an activation button and is disposed in angular registration with the handle such that proximal movement of the handle towards a fully actuated position operably engages the activation button to activate the switch. In still other aspects according to the present disclosure, the activation button is configured to engage a mechanical interface disposed within the housing, the mechanical interface configured to generate a response to engagement with the activation button. The response may be tactile and/or audible.

The present disclosure also relates to a method for sealing tissue using a surgical instrument and includes: actuating a handle towards a housing of a surgical instrument to move front and rear drive tubes to close a first jaw member and a second jaw member to grasp tissue; further actuating the handle beyond the initial movement of the handle in the same direction to move the rear drive tube relative to the front drive tube and pull a front washer proximally forcing a stopper tube to slide proximally towards a rear washer to eliminate a dead space between the rear washer and the stopper tube; and further actuating the handle towards the housing to compress a jaw force spring and move a spring collar disposed atop the rear drive tube to provide a closure force between the first and second jaw members.

In aspects according to the present disclosure, the method further includes further actuating the handle towards the housing to activate a switch disposed in the housing to provide electrosurgical energy to the jaw members to seal tissue disposed therebetween. In other aspects according to the present disclosure, the closure force is provided within the range of about 3 kg/cm$^2$ to about 15 kg/cm$^2$.

In aspects according to the present disclosure, the method further includes: further actuating the handle towards the housing to engage an activation button disposed in angular registration with the handle, the activation button generating a response to engagement with the handle; and further actuating the handle to depress the activation button to activate a switch to provide electrosurgical energy to the jaw members to seal tissue disposed therebetween. In aspects according to the present disclosure, the response is tactile and/or audible.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 3A is a perspective view of the end effector and elongated shaft of FIG. 1 with parts separated;

FIG. 3B is cross-sectional view taken along line 3B-3B of FIG. 3A showing a distal portion of the electrosurgical forceps of FIG. 1 depicting a tube guide;

FIG. 12A is a perspective view of a proximal portion of the knife actuation mechanism of the end effector of FIG. 1;

FIG. 12B is a cross-sectional, side view of a knife collar of the knife actuation mechanism of the end effector of FIG. 1;

FIG. 13A is a side view of the proximal portion of the instrument of FIG. 10 depicting a movable handle in a separated position with respect to a stationary handle, which corresponds to the open configuration of the end effector depicted in FIG. 2A, and a knife trigger in a separated configuration with respect to the stationary handle, which corresponds to an un-actuated or proximal configuration of a knife with respect to the jaw members;

FIG. 13B is a side view of the proximal portion of the instrument of FIG. 10 depicting the movable handle in an intermediate position with respect to the stationary handle, which corresponds to a first closed configuration of the end effector wherein the jaw members encounter one another;

FIG. 13C is a side view of the proximal portion of the instrument of FIG. 10 depicting the movable handle in an approximated configuration with respect to the stationary handle, which corresponds to a second closed configuration of the end effector wherein the jaw members apply an appropriate pressure to generate a tissue seal;

FIG. 13D is a side view of the proximal portion of the instrument of FIG. 10 depicting the knife trigger in an actuated configuration, which corresponds to an actuated or distal position of the knife with respect to the jaw members;

DETAILED DESCRIPTION

Figure 1:
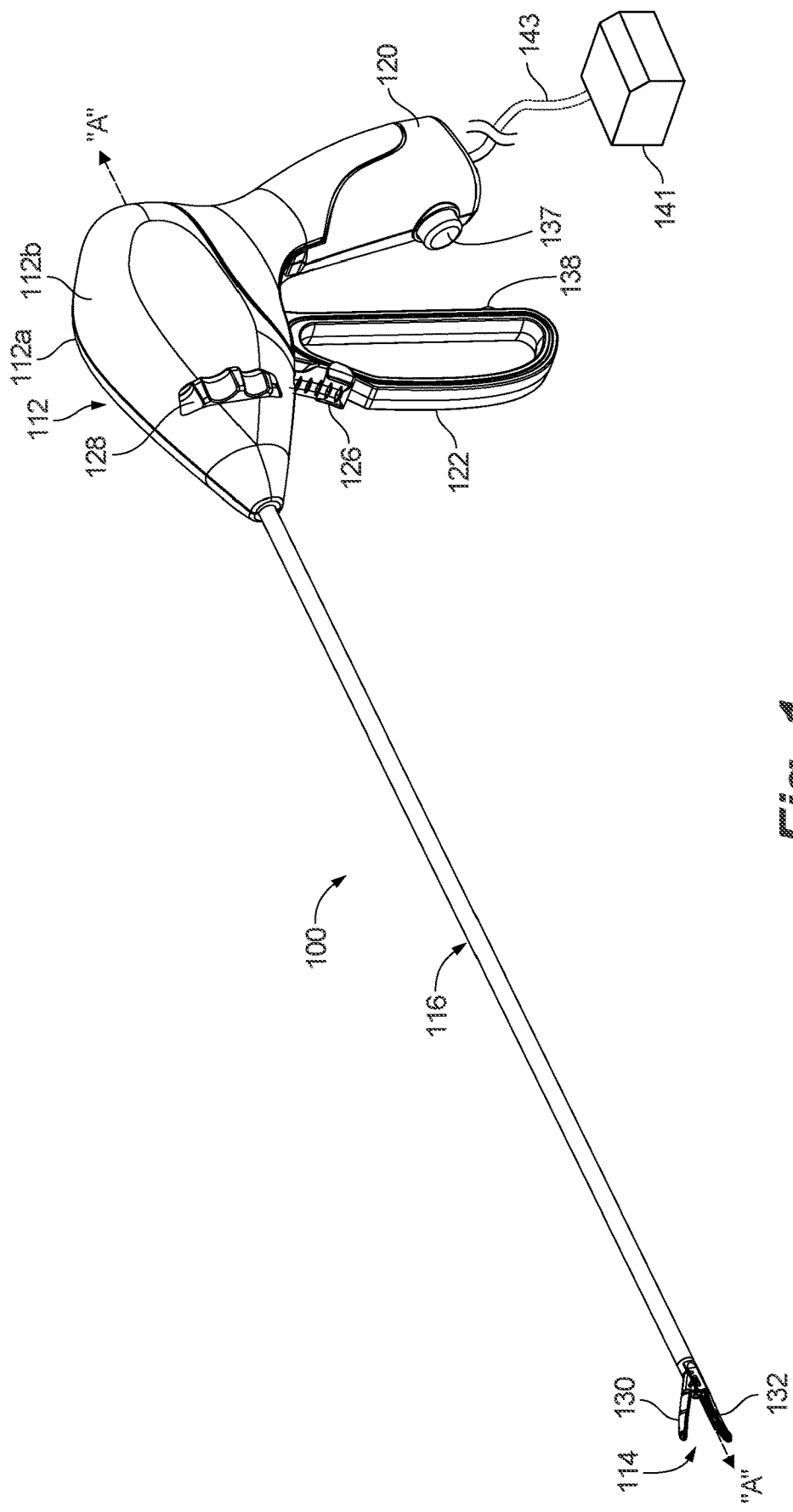
FIG. 1 is a perspective view of an electrosurgical forceps according to an embodiment of the present disclosure including a housing, an elongated shaft, and an end effector.

Referring initially to FIG. 1, an electrosurgical forceps 100 generally includes a housing 112 that supports various actuators thereon for remotely controlling an end effector 114 through an elongated shaft 116. Although this configuration is typically associated with instruments for use in laparoscopic or endoscopic surgical procedures, various aspects of the present disclosure may be practiced with traditional open instruments and in connection with endoluminal procedures as well. The housing 112 is constructed of a left housing half 112a and a right housing half 112b. The left and right designation of the housing halves 112a, 112b refer to the respective directions as perceived by an operator using the forceps 100. The housing halves 112a, 112b may be constructed of sturdy plastic, and may be joined to one another by adhesives, ultrasonic welding or other suitable assembly methods.

To mechanically control the end effector 114, the housing 112 supports a stationary handle 120, a movable handle 122, a trigger 126 and a rotation knob 128. The movable handle 122 is operable to move the end effector 114 between an open configuration (FIG. 2A) wherein a pair of opposed jaw members 130, 132 are disposed in spaced relation relative to one another, and a closed or clamping configuration (FIG. 2B) wherein the jaw members 130, 132 are closer together. Approximation of the movable handle 122 with the stationary handle 120 serves to move the end effector 114 to the closed configuration and separation of the movable handle 122 from the stationary handle 120 serves to move the end effector 114 to the open configuration. The trigger 126 is operable to extend and retract a knife blade 156 (see FIGS. 2A and 2B) through the end effector 114 when the end effector 114 is in the closed configuration. The rotation knob 128 serves to rotate the elongated shaft 116 and the end effector 114 about a longitudinal axis A-A extending through the forceps 114.

To electrically control the end effector 114, the stationary handle 120 supports a depressible button 137 thereon, which is operable by the user to initiate and terminate the delivery of electrosurgical energy to the end effector 114. The depressible button 137 is mechanically coupled to a switch (not shown) disposed within the stationary handle 120 which is in electrical communication with an electrosurgical generator 141 via suitable electrical wiring (not explicitly referenced) extending from the housing 112 through a cable 143 extending between the housing 112 and the electrosurgical generator 141. The generator 141 may include devices such as the LigaSure® Vessel Sealing Generator and the ForceTriad® Generator sold by Covidien. The cable 143 may include a connector (not shown) thereon such that the forceps 100 may be selectively coupled electrically to the generator 141.

Figure 2A:
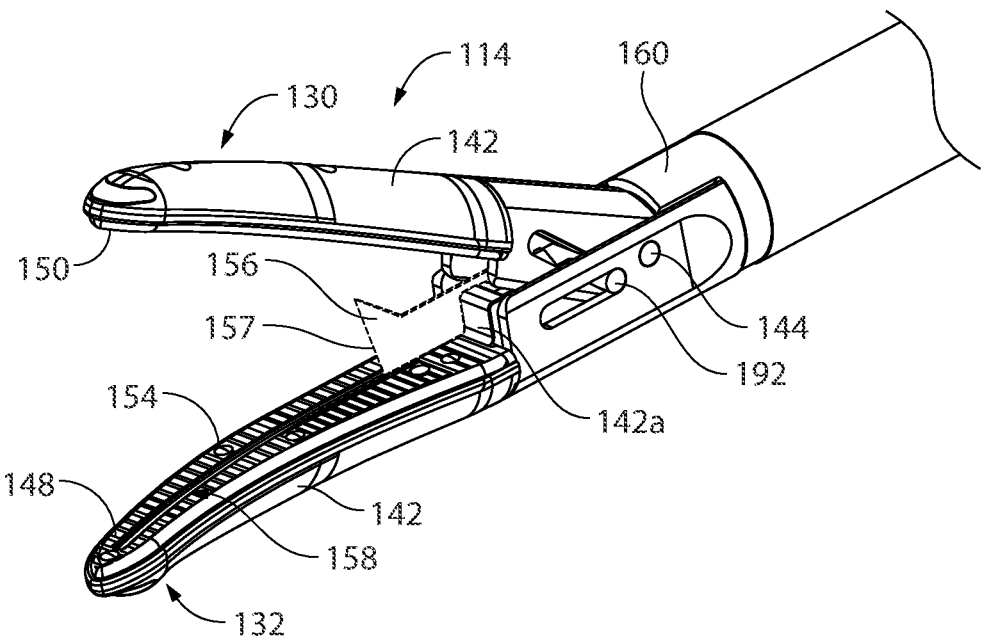
FIG. 2A is an enlarged, perspective view of the end effector of FIG. 1 depicted with a pair of jaw members in an open configuration.
Figure 2B:
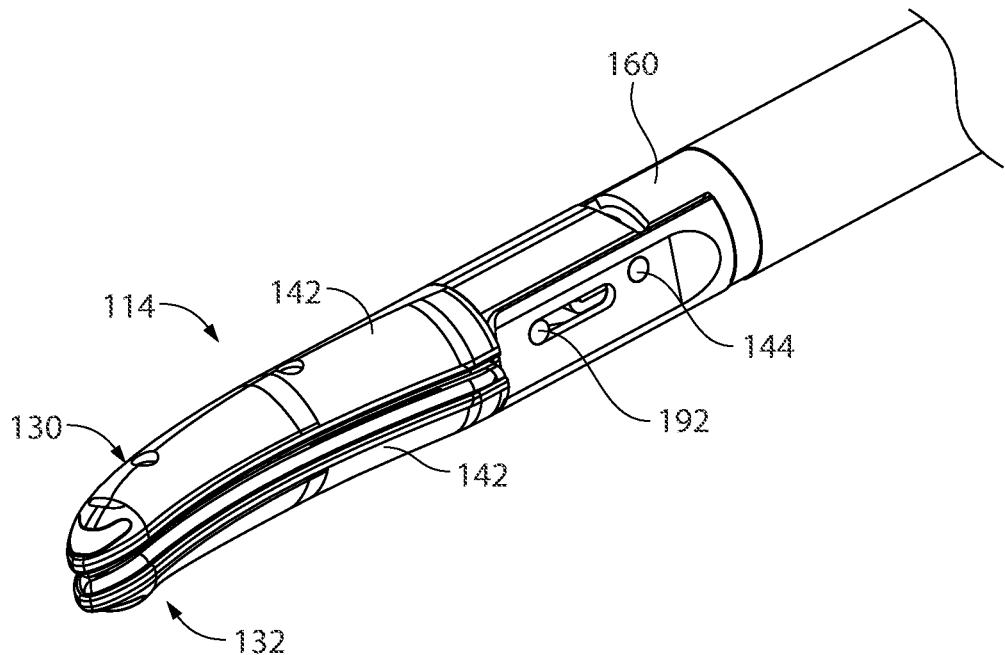
FIG. 2B is an enlarged, perspective view of the end effector of FIG. 1 depicted with the pair of jaw members in a closed configuration.
Figure 4:
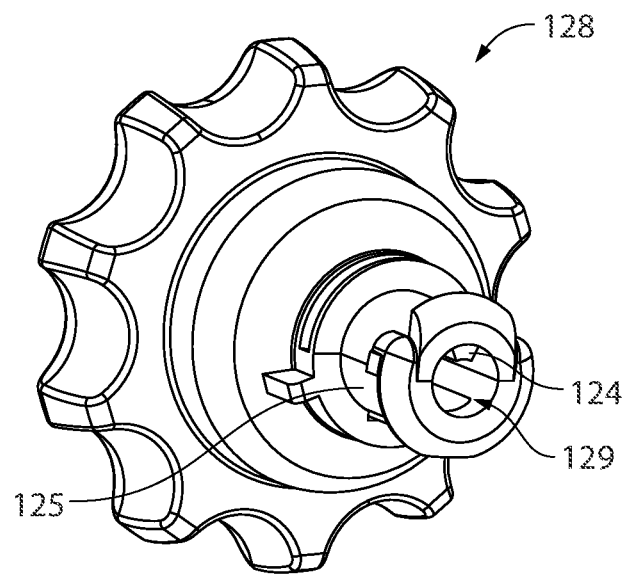
FIG. 4 is a proximally-facing, perspective view of a rotation knob depicting a passageway for receiving the elongated shaft of FIG. 1.
Figure 5:
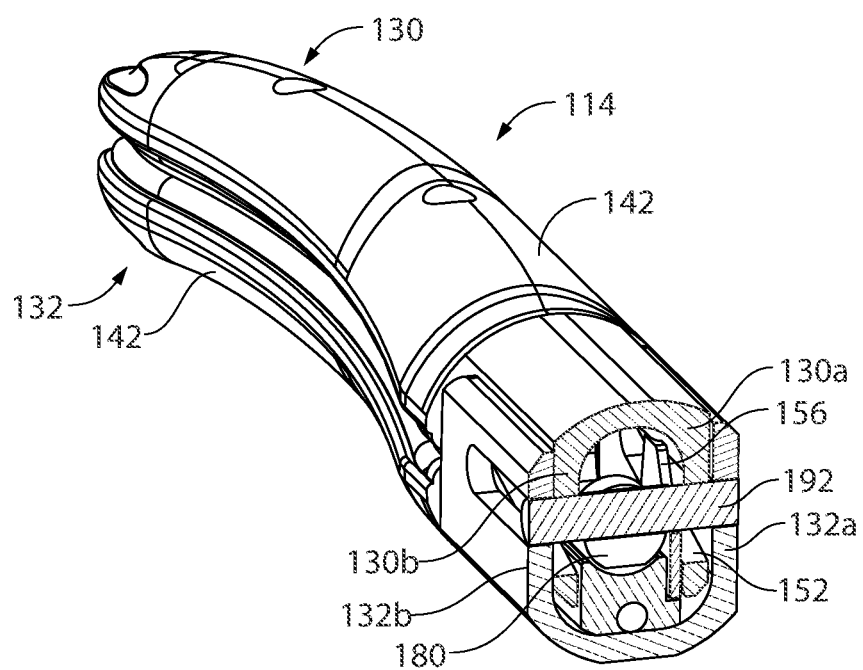
FIG. 5 is a cross-sectional, perspective view of the end effector of FIG. 1.

Referring now to FIGS. 2A-2B, the end effector 114 may be moved from the open configuration (FIG. 2A) wherein tissue (not shown) is received between the jaw members 130, 132, and the closed configuration (FIG. 2B), wherein the tissue is clamped and treated. The jaw members 130, 132 pivot about a pivot pin 144 to move the end effector 114 to the closed configuration of FIG. 2B wherein the sealing plates 148, 150 provide a pressure to tissue grasped therebetween. In some embodiments, to provide an effective tissue seal, a pressure within a range between about 3 $kg/cm^2$ to about 16 $kg/cm^2$ and, desirably, within a working range of about 7 $kg/cm^2$ to about 13 $kg/cm^2$, may be applied to the tissue. Also, in the closed configuration, a separation or gap distance is maintained between the sealing plates 148, 150 by an array of stop members 154 (FIG. 2A) disposed on or adjacent the sealing plates 148, 150. The stop members 154 contact opposing surfaces on the opposing jaw member 130, 132 and prohibit further approximation of the sealing plates 148, 150. In some embodiments, to provide an effective tissue seal, an appropriate gap distance of about 0.001 inches to about 0.010 inches and, desirably, between about 0.002 inches to about 0.005 inches, may be provided. In some embodiments, the stop members 154 are constructed of a heat-resistant ceramic deposited onto the jaw members 130, 132. In other embodiments, the stop members 154 are constructed of an electrically non-conductive plastic molded onto the jaw members 130, 132, e.g., by a process such as overmolding or injection molding.

The upper and lower jaw members 130, 132 are electrically coupled to cable 143, and thus to the generator 141 (e.g., via respective suitable electrical wiring extending through the elongated shaft 116) to provide an electrical pathway to a pair of electrically conductive, tissue-engaging sealing plates 148, 150 disposed on the lower and upper jaw members 132, 130, respectively. The sealing plate 148 of the lower jaw member 132 opposes the sealing plate 150 of the upper jaw member 130. In some embodiments, the sealing plates 148 and 150 are electrically coupled to opposite terminals, e.g., positive or active (+) and negative or return (−) terminals associated with the generator 141. Thus, bipolar energy may be provided through the sealing plates 148 and 150 to tissue. Alternatively, the sealing plates 148 and 150 may be configured to deliver monopolar energy to tissue. In a monopolar configuration, one or both sealing plates 148 and 150 deliver electrosurgical energy from an active terminal, e.g., (+), while a return pad (not shown) is placed generally on a patient and provides a return path to the opposite terminal, e.g., (−), of the generator 141. Each jaw member 130, 132 includes a jaw insert (not shown) and an insulator (not shown) that serves to electrically insulate the sealing plates 150, 148 from the jaw insert of the jaw members 130, 132, respectively.

Electrosurgical energy may be delivered to the tissue through the electrically conductive seal plates 148, 150 to effect a tissue seal. Once a tissue seal is established, a knife blade 156 having a sharpened distal edge 157 may be advanced through a knife channel 158 defined in one or both jaw members 130, 132 to transect the sealed tissue. Although the knife blade 156 is depicted in FIG. 2A as extending from the elongated shaft 116 when the end effector 114 is in an open configuration, in some embodiments, extension of the knife blade 156 into the knife channel 158 when the end effector 114 is in the open configuration may be prevented by one or more lockout features.

Referring to FIG. 3A, the elongated shaft 116 includes various longitudinal components that operatively couple the end effector 114 to the various actuators supported by the housing 112 (FIG. 1). An outer shaft member 160 defines an exterior surface of the elongated shaft 116 and houses other components therein as described below. The outer shaft member 160 is configured for longitudinal motion with respect to an inner actuation member 180 axially received within the outer shaft member 160. The inner actuation member 180 may be a rod, a shaft, a tube, folded metal, stamped metal, or other suitable structure. A proximal portion 166 of the outer shaft member 160 is configured for receipt within the housing 112 (FIG. 1), and includes features for operatively coupling the outer shaft member 160 to various elements of the housing 112. More specifically, the proximal portion 166 of the outer shaft member 160 includes, in order from distal to proximal, a longitudinal slot 169 to couple the outer shaft member 160 to the rotation knob 128, a longitudinal knife slot 168 defined therethrough, a pair of opposing distal locking slots 161a, 161b, and a pair of opposing proximal locking slots 171a, 171b.

Figure 10:
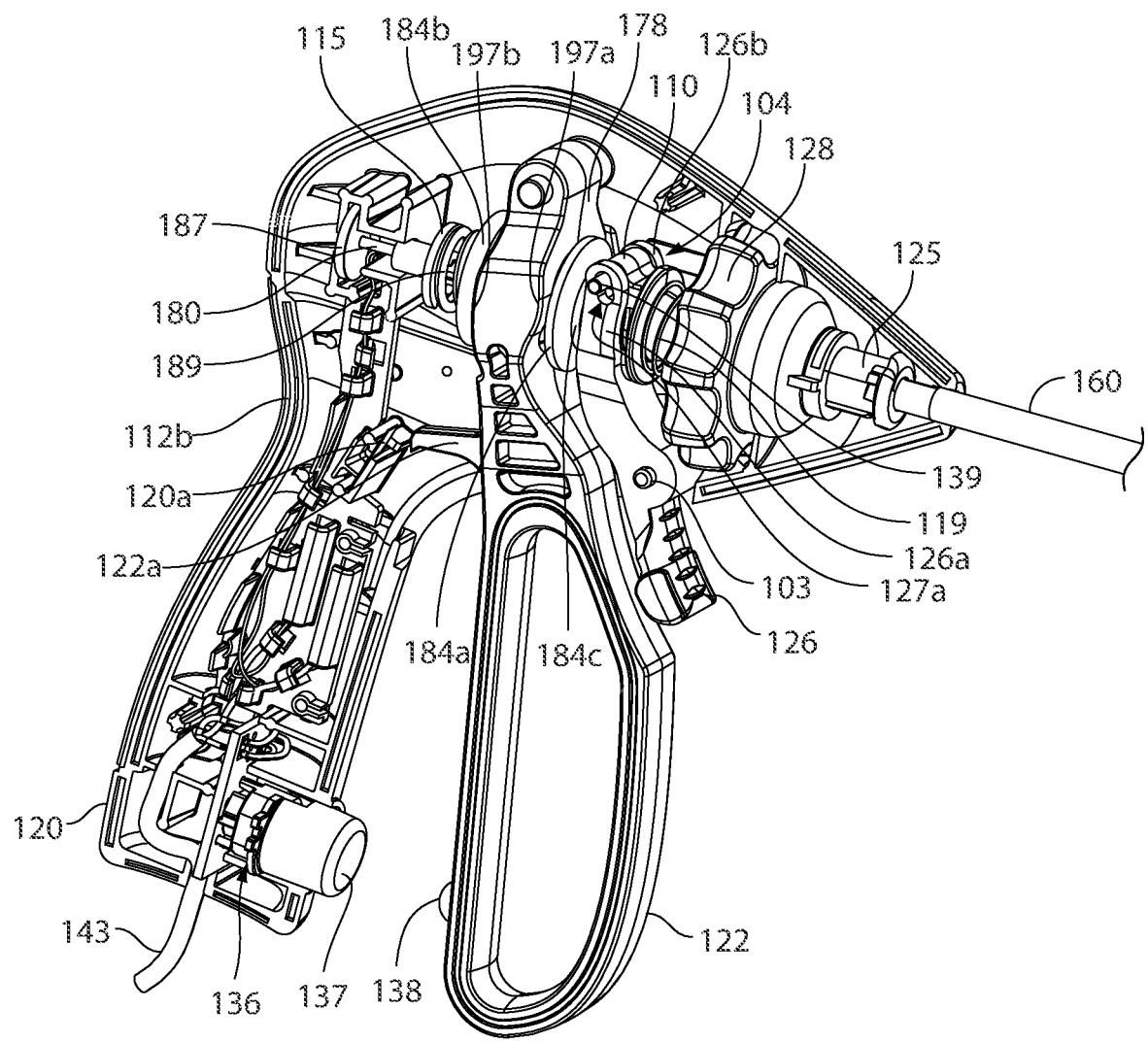
FIG. 10 is a perspective view of a proximal portion of the instrument of FIG. 1 with a portion of the housing removed revealing internal components.

A distal portion 186 of the inner actuation member 180 includes a longitudinal recess 190 defined therein that provides clearance for the pivot pin 144 and thus, permits longitudinal reciprocation of the pivot pin 144 (via longitudinal reciprocation of the outer shaft member 160) independent of the inner actuation member 180. Distally of the longitudinal recess 190, a cam pin 192 is mechanically coupled (e.g., via welding, friction-fit, laser welding, etc) to the distal portion 186 of the inner actuation member 180. A proximal portion 188 of the inner actuation member 180 includes a washer 187 coupled thereto (FIG. 10). The washer 187 is captured within the housing 112 and serves to prohibit longitudinal motion of the inner actuation member 180 parallel to the longitudinal axis A-A.

The pivot pin 144 extends through a proximal portion of each of the jaw members 130, 132 to pivotally support the jaw members 130, 132 at the distal end of the inner actuation member 180. A proximal portion of each of the jaw members 130, 132 includes two laterally spaced parallel flanges or "flags" 130a, 130b and 132a, 132b respectively, extending proximally from a distal portion of the jaw members 130 and 132. A lateral cam slot 130c and a lateral pivot bore 130d extend through each of the flags 130a, 130b of the upper jaw member 130. Similarly, a lateral cam slot 132c and a lateral pivot bore 132d extend through each of the flags 132a, 132b of the lower jaw member 132. The pivot bores 130d, 132d receive the pivot pin 144 in a slip-fit relation that permits the jaw members 130, 132 to pivot about the pivot pin 144 to move the end effector 114 between the open and closed configurations (FIGS. 2A and 2B, respectively).

A knife rod 102 is coupled (e.g., via welding) at a distal-most end to the sharpened knife blade 156 and includes an angled proximal end 108 that provides a mechanism for operatively coupling the knife rod 102 to the trigger 126. In some embodiments, the angled proximal end 108 of the knife rod 102 is formed by bending the knife rod 102 ninety degrees at its proximal end during manufacturing. The sharpened distal edge 157 of the knife blade 156 may be applied to the distal end of the knife blade 156 using a variety of manufacturing techniques such as, for example, grinding, coining, electrochemical etching, electropolishing, or other suitable manufacturing technique, for forming sharpened edges.

The outer shaft member 160 may be drawn proximally relative to the inner actuation member 180 and the cam pin 192 to move the end effector 114 to the closed configuration (see FIG. 2B). Since the longitudinal position of the cam pin 192 is fixed, and since the cam slot 130c is obliquely arranged with respect to the longitudinal axis A-A, proximal retraction of the outer shaft member 160 induces distal translation of the cam pin 192 through the cam slots 130c, 132c such that the jaw member 130 pivots toward jaw member 132 about the pivot pin 144. Conversely, when the end effector 114 is in the closed configuration, longitudinal translation of the outer shaft member 160 in a distal direction induces proximal translation of the cam pin 192 through the cam slots 130c, 132c such that jaw member 130 pivots away from jaw member 132 toward the open configuration.

In some embodiments, the inner actuation member 180 may be configured to move relative to the outer shaft member 160 to move the end effector 114 between the open and closed configurations. In this scenario, the moveable handle 122 may be operably coupled to the inner actuation member 180 and the washer 187 coupled to the proximal portion 188 of the inner actuation member 180 may be removed such that the inner shaft member 180 is free to move longitudinally along the longitudinal axis A-A upon actuation of the moveable handle 122. Proximal retraction of the inner actuation member 180 may induce proximal translation of the cam pin 192 through the cam slots 130c, 132c such that the jaw member 130 pivots away from jaw member 132 about the pivot pin 144 toward the open configuration. Conversely, when the end effector 114 is in the open configuration, longitudinal translation of the inner actuation member 180 in a distal direction induces distal translation of the cam pin 192 through the cam slots 130c, 132c such that jaw member 130 pivots toward jaw member 132 toward the closed configuration.

Referring now to FIGS. 10, 12A, 12B and 13A-13D, the connection of the movable handle 122 and the knife trigger 126 to the longitudinally movable components of the elongated shaft 116 is described. The movable handle 122 may be manipulated to impart longitudinal motion to the outer shaft member 160, and the knife trigger 126 may be manipulated to impart longitudinal motion to the knife rod 102. As discussed above, longitudinal motion of the outer shaft member 160 serves to move the end effector 114 between the open configuration of FIG. 2A and the closed configuration of FIG. 2B, and longitudinal motion of the knife rod 102 serves to move knife blade 156 through knife channel 158 (FIG. 2A).

Figure 11:
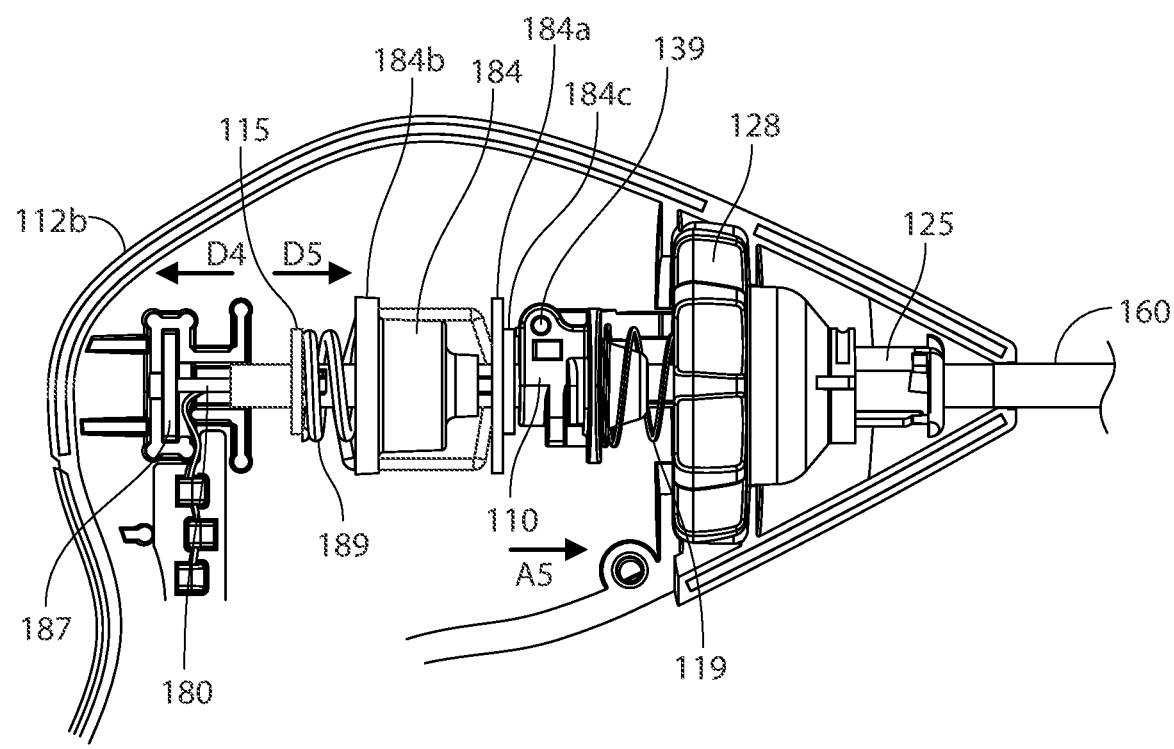
FIG. 11 is a partial, side view of a proximal portion of the instrument of FIG. 1.

The movable handle 122 is operatively coupled to the outer shaft member 160 by a clevis 178 defined at an upper end of the movable handle 122. The clevis 178 is pivotally supported on the housing 112. The clevis 178 extends upwardly about opposing sides of a drive collar 184 (FIG. 11) supported on the outer shaft member 160 and includes rounded drive surfaces 197a and 197b thereon. Drive surface 197a engages a proximal-facing surface of a distal spring washer 184a and drive surface 197b engages a distal facing surface of a proximal rim 184b of the drive collar 184 (FIG. 11). The distal spring washer 184a engages a proximal facing surface of a distal spring stop 184c that, in turn, engages the opposing distal locking slots 161a, 161b (FIG. 3A) extending through the proximal portion 166 (FIG. 3A) of the outer shaft member 160 to couple the distal spring stop 184c to the outer shaft member 160. The drive surfaces 197a, 197b are arranged along the longitudinal axis A-A such that pivotal motion of the movable handle 122 induces corresponding longitudinal motion of the drive collar 184 (FIG. 11) along the longitudinal axis A-A.

Referring now to FIG. 11, proximal longitudinal motion may be imparted to the outer shaft member 160 by pushing the proximal rim 184b of the drive collar 184 proximally with the movable handle 122 (FIG. 10) as indicated by arrow D4 (FIG. 11). A spring 189 is constrained between a proximal facing surface of the drive collar 184 and a proximal spring stop 115. The proximal spring stop 115 engages the opposing proximal locking slots 171a, 171b (FIG. 3A) extending through the proximal portion 166 (FIG. 3A) of the outer shaft member 160 to couple the proximal spring stop 115 to the outer shaft member 160. Thus, the proximal spring stop 115 serves as a proximal stop against which spring 189 compresses.

Distal longitudinal motion is imparted to the outer shaft member 160 by driving the drive collar 184 distally with the movable handle 122. Distal longitudinal motion of the drive collar 184 induces a corresponding distal motion of the outer shaft member 160 by virtue of the coupling of the drive collar 184 to opposing distal locking slots 181a, 181b extending through the proximal portion 166 of the outer shaft member 160 (FIG. 3A).

Figure 6:
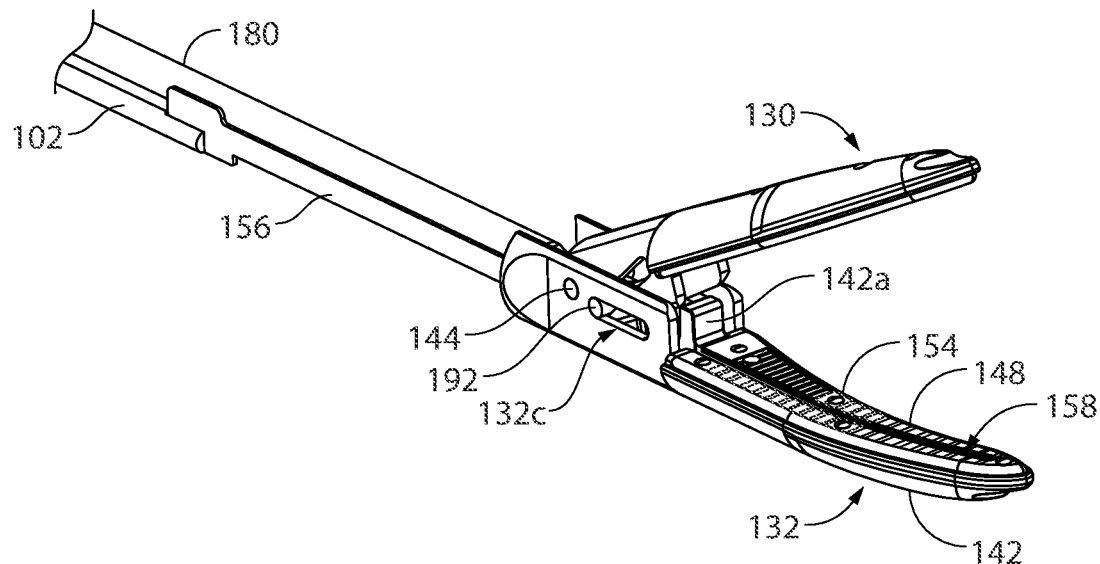
FIG. 6 is a partial, proximal-facing perspective view of a distal portion of a jaw actuation mechanism of the end effector of FIG. 1.
Figure 7:
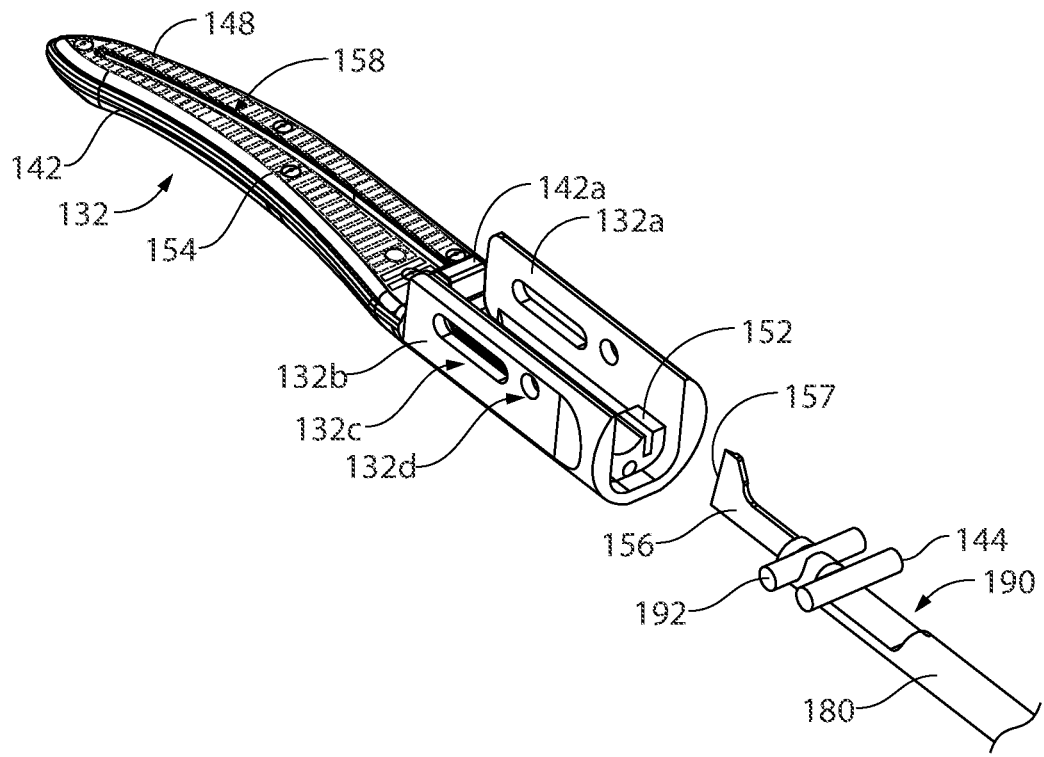
FIG. 7 is a partial, distal-facing perspective view of distal portion of a knife actuation mechanism of the end effector of FIG. 1.
Figures 8, 9:
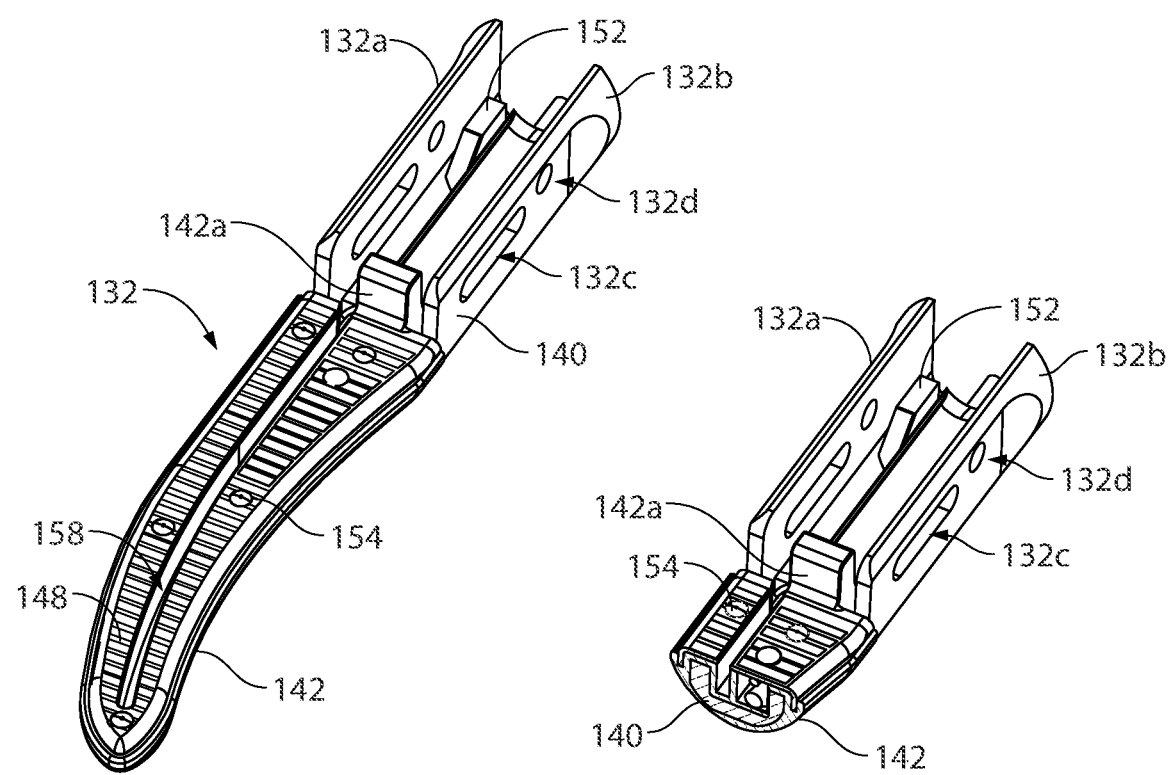
FIG. 8 is a perspective view of a lower jaw member of the end effector of FIG. 1.
FIG. 9 is a cross-sectional, perspective view of the lower jaw member of FIG. 8.

Proximal longitudinal motion of the outer shaft member 160 draws jaw member 132 proximally such that the cam pin 192 advances distally to pivot jaw member 130 toward jaw member 132 to move the end effector 114 to the closed configuration as described above with reference to FIG. 6. Once the jaw members 130 and 132 are closed, the outer shaft member 160 essentially bottoms out (i.e., further proximal movement of the outer shaft member 160 is prohibited since the jaw members 130, 132 contact one another). Further proximal movement of the movable handle 122 (FIG. 10), however, will continue to move the drive collar 184 proximally. This continued proximal movement of the drive collar 184 further compresses the spring 189 to impart additional force to the outer shaft member 160, which results in additional closure force applied to tissue grasped between the jaw members 130, 132 (see FIG. 2B).

Referring again to FIG. 10, the trigger 126 is pivotally supported in the housing 112 about a pivot boss 103 protruding from the trigger 126. The trigger 126 is operatively coupled to the knife rod 102 by a knife connection mechanism 104 such that pivotal motion of the trigger 126 induces longitudinal motion of the knife rod 102. The knife connection mechanism 104 includes upper flanges 126a, 126b of the trigger 126 and a knife collar 110.

Referring now to FIGS. 11, 12A, and 12B, the knife collar 110 includes a pair of integrally formed pin bosses 139a, 139b extending from opposing sides thereof. As shown by FIG. 12B, the knife collar 110 includes an interior circular channel 113 that captures the angled proximal end 108 of the knife rod 102 to couple the knife rod 102 to the knife collar 110. Upon longitudinal motion of the outer shaft member 160, the angled proximal end 108 of the knife rod 102 translates longitudinally within knife slot 168 (FIG. 3A) of the outer shaft member 160 such that the longitudinal motion of outer shaft member 160 is unimpeded by the angled proximal end 108 of the knife rod 102. Upon rotation of the elongated shaft 116 and end effector 114 about the longitudinal axis A-A via the rotation knob 128 (FIG. 1), the angled proximal end 108 of the knife rod 102 freely rotates within the interior circular channel 113 of the knife collar 110 such that the outer and inner actuation members 160 and 180 (removed from view in FIG. 12B for clarity), and the knife rod 102 rotate within the knife collar 110 about the longitudinal axis A-A. In this way, the knife collar 110 serves as a stationary reference for the rotational movement of the outer shaft member 160, the inner actuation member 180, and the knife rod 102.

Referring again to FIG. 10, the upper flanges 126a, 126b of the trigger 126 include respective slots 127a, 127b defined therethrough that are configured to receive the pin bosses 139a, 139b, respectively, of the knife collar 110 such that pivotal motion of the trigger 126 induces longitudinal motion of the knife collar 110 and, thus, the knife rod 102 by virtue of the coupling of knife rod 102 to the knife collar 110.

Referring now to FIGS. 11 and 12A, when the trigger 126 is moved to induce motion of the knife collar 110 in order to translate the blade 156 through the knife channel 158, the knife collar 110 translates along the outer shaft member 160 in the direction of arrow A5 to abut a spring 119 such that spring 119 compresses against the distal portion 125 of the rotation knob 128 (FIG. 12A). The spring 119 biases the knife collar 110 proximally along the outer shaft member 160.

Referring now to FIGS. 13A, 13B, 13C and 13D, a sequence of motions may be initiated by moving the movable handle 122 to induce motion of the outer shaft member 160 in order to close the jaws 130, 132, and by moving the trigger 126 to induce motion of the knife collar 110 in order to translate the blade 156 through the knife channel 158. Initially, both the moveable handle 122 and the knife trigger 126 are in a distal or un-actuated position as depicted in FIG. 13A. This arrangement of the moveable handle 122 and trigger 126 sustains the end effector 114 in the open configuration (FIG. 2A) wherein the jaw members 130, 132 are substantially spaced from one another, and the knife blade 156 is in a retracted or proximal position with respect to the jaw members 130, 132. When both the moveable handle 122 and the knife trigger 126 are in the distal, un-actuated position, pivotal motion of the knife trigger 126 in a proximal direction, i.e., toward the stationary handle 120, is passively prohibited by interference between the trigger 126 and moveable handle 122. This interference prohibits advancement of the knife blade 156 through the knife channel 158 when the end effector 114 is in the open configuration.

The movable handle 122 may be moved from the distal position of FIG. 13A to the intermediate position depicted in FIG. 13B to move the jaw members 130, 132 to the closed configuration (FIG. 2B). As the movable handle 122 pivots in the direction of arrow M1 (FIG. 13B), the drive surface 197b of the movable handle 122 engages the proximal rim 184b of the drive collar 184. The drive collar 184 is driven proximally such that the spring 189 biases the proximal spring stop 115 and, thus, the outer shaft member 160 is driven proximally in the direction of arrow M2 (FIG. 13B). As discussed above with reference to FIG. 6, proximal movement of the outer shaft member 160 serves to translate the cam pin 192 distally though the cam slots 130c, 132c (FIG. 3A) of the jaw members 130, 132, respectively, and thus pivot jaw member 130 toward jaw member 132 (FIG. 2B). As the jaw members 130, 132 engage one another and no further pivotal movement of the jaw members 130, 132 may be achieved, further distal movement of the cam pin 192 and further proximal movement of the outer shaft member 160 are prevented.

As the movable handle 122 is moved from the distal position of FIG. 13A to the intermediate position depicted in FIG. 13B, a tooth 122a extending proximally from an upper portion of the moveable handle 122 engages a clicker tab 120a supported within the stationary handle 120 to generate a tactile and/or an audible response. The clicker tab 120a may be constructed of a plastic film, sheet metal, or any suitable material configured to generate a "clicking" sound as the clicker tab 120a is engaged and disengaged by the tooth 122a. This response generated by the clicker tab 120a corresponds to a complete grasping of tissue between the jaw members 130, 132 and serves to indicate to the surgeon that further pivotal motion of the moveable handle 122 in a proximal direction, i.e., toward the stationary handle 120, will cause the button activation post 138 to engage the depressible button 137. As the moveable handle 122 is moved from the intermediate position of FIG. 13B to the actuated or proximal position of FIG. 13C, the button activation post 138 depresses the depressible button 137, thereby activating the switch 136 disposed within the stationary handle 120 to initiate the delivery of electrosurgical energy to the end effector 114 to generate a tissue seal.

As the movable handle 122 is moved from the intermediate position of FIG. 13B to the actuated or proximal position of FIG. 13C, the pressure applied by the jaw members 130, 132 is increased. As the movable handle 122 pivots further in the direction of arrow M3 (FIG. 13C), the drive surface 197b presses the proximal rim 184b of the drive collar 184 further proximally against the spring 189 in the direction of arrow M4 (FIG. 13C). The spring 189 is compressed against the proximal spring stop 115, and a tensile force is transmitted through the outer shaft member 160 to the jaw members 130, 132. The tensile force supplied by the spring 189 ensures that the jaw members 130, 132 apply an appropriate pressure to effect a tissue seal.

When the movable handle 122 is in the actuated or proximal position, the knife trigger 126 may be selectively moved from the distal position of FIG. 13C to the proximal position of FIG. 13D to advance the knife blade 156 distally through knife channel 158. The knife trigger 126 may be pivoted in the direction of arrow M5 (FIG. 13D), about pivot boss 103 to advance the flanges 126a, 126b of the knife trigger 126 distally in the direction of arrow M6 such that the pin bosses 139a, 139b translate within respective slots 127a, 127b from the position shown in FIGS. 13A-13C to the position shown in FIG. 13D (flange 126b, pin boss 139b, and slot 127b are obstructed from view in FIGS. 13A-13D).

Movement of flanges 126a, 126b draws the knife collar 110 distally, which induces distal longitudinal motion of the knife rod 102 by virtue of the coupling of the knife rod 102 to the knife collar 110, as described above with reference to FIG. 12B.

FIGS. 14A-17D show an alternate embodiment of an electrosurgical forceps 1000 according to the present disclosure. Forceps 1000 includes similar elements to forceps 10 and, as such, similar reference numbers are used to describe the various components thereof and the relative movements of the various components as they relate to operation of the forceps 1000. More particularly, forceps 1000 is configured to provide a so called "dead space" between initial actuation of the movable handle 1122 to close the jaw members 1130, 1132 and full actuation of handle 1122 to depress activation button 137 to energize the forceps 1000.

More particularly and with initial respect to FIGS. 14A-14D, forceps 1000 includes a housing 1112 having a stationary handle 1120, a movable handle 1122 and an elongated shaft 1116 that extends therefrom configured to support an end effector assembly 1114 at a distal end thereof. End effector assembly 1114 includes opposing first and second jaw members, 1130, 1132 that are selectively movable relative to one another for an initial open positon relative to one another to a closed position for grasping tissue therebetween via actuation of movable handle 1122.

Movable handle 1122 includes a clevis 1178 that is pivotably coupled to housing 1112 about a pivot 1178a. Clevis 1178 of movable handle 1122 operably couples to a drive assembly 1125 that, upon actuation of movable handle 1122 relative to stationary handle 1120, transitions the jaw members 1130, 1132 of end effector assembly 1114 between the open and closed positons. More particularly, clevis 1178 includes front and rear drive surfaces 1197a, 1197b that cooperate with the drive assembly 1125 to move the jaw members 1130, 1132. Front drive surface 1197a operably engages a distal spring washer 1184a that secures to housing 1112 and rear drive surface 1197b (or a portion thereof) operably couples to a spring collar 1126 that slidingly mounts atop the rear drive tube 1160. A jaw force spring or compression spring 1189 is disposed atop rear tube 1160 and biases the spring collar 1126 against a rear stop 1115. As explained in more detail below, actuation of the movable handle 1122 through its range of motion will ultimately bias the jaw force spring 1189 which, in turn, provides a closure force to the jaw members 1130, 1132.

Figure 14A:
FIG. 14A is an internal, side view of an electrosurgical forceps according to another embodiment of the present disclosure including a housing, an elongated shaft, a movable handle, and an end effector assembly shown in an open configuration.
Figure 14B:
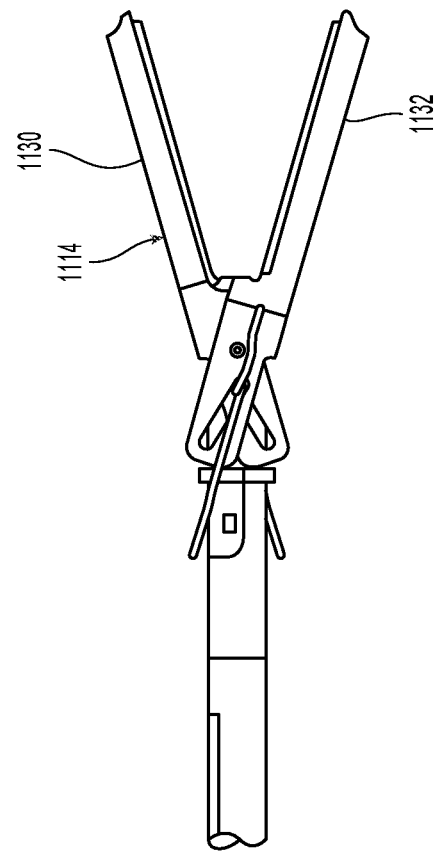
FIG. 14B is an enlarged view of the end effector assembly of the electrosurgical forceps of FIG. 14A.
Figure 14C:
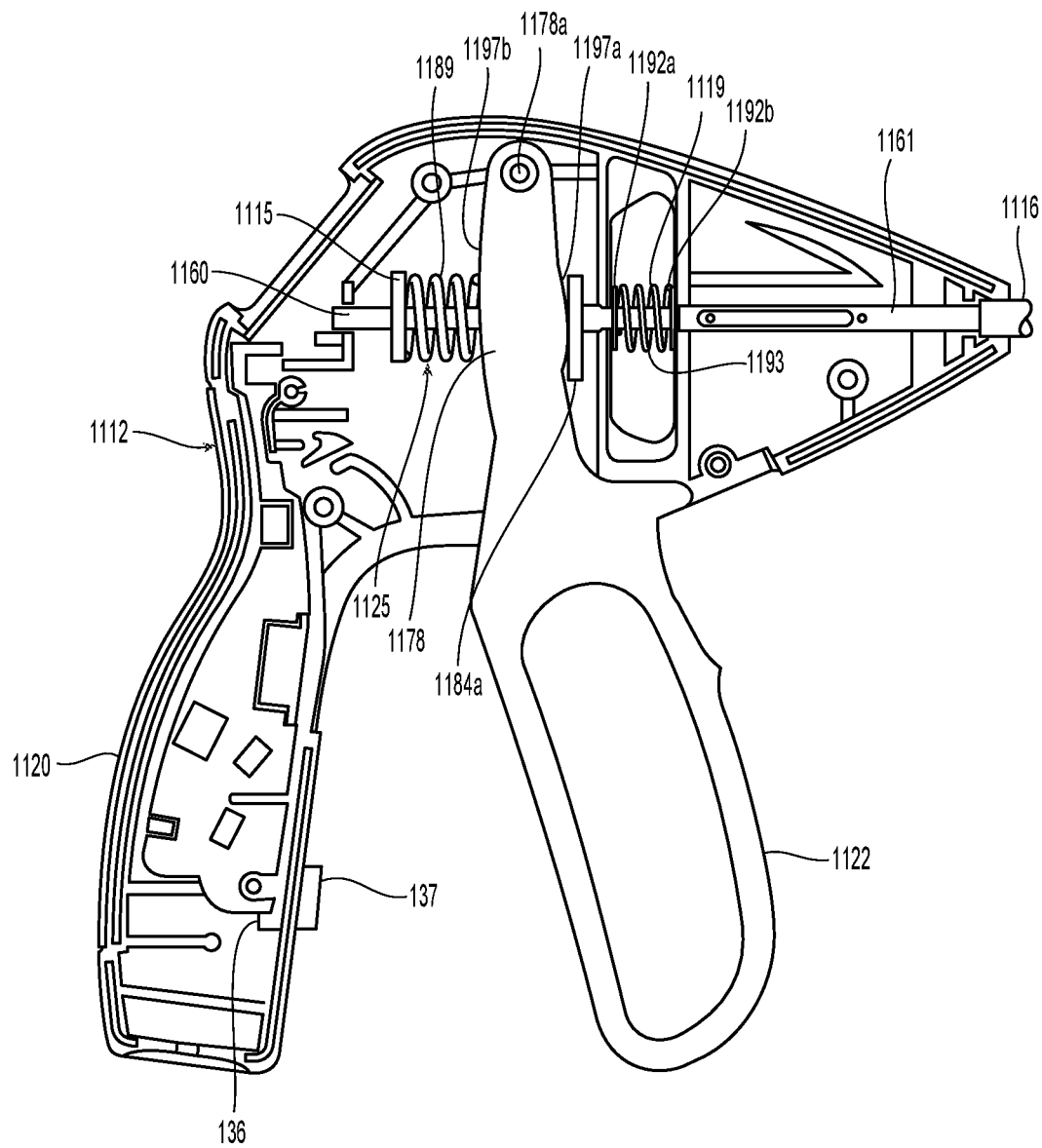
FIG. 14C is an enlarged view of the electrosurgical forceps of FIG. 14A.
Figure 14D:
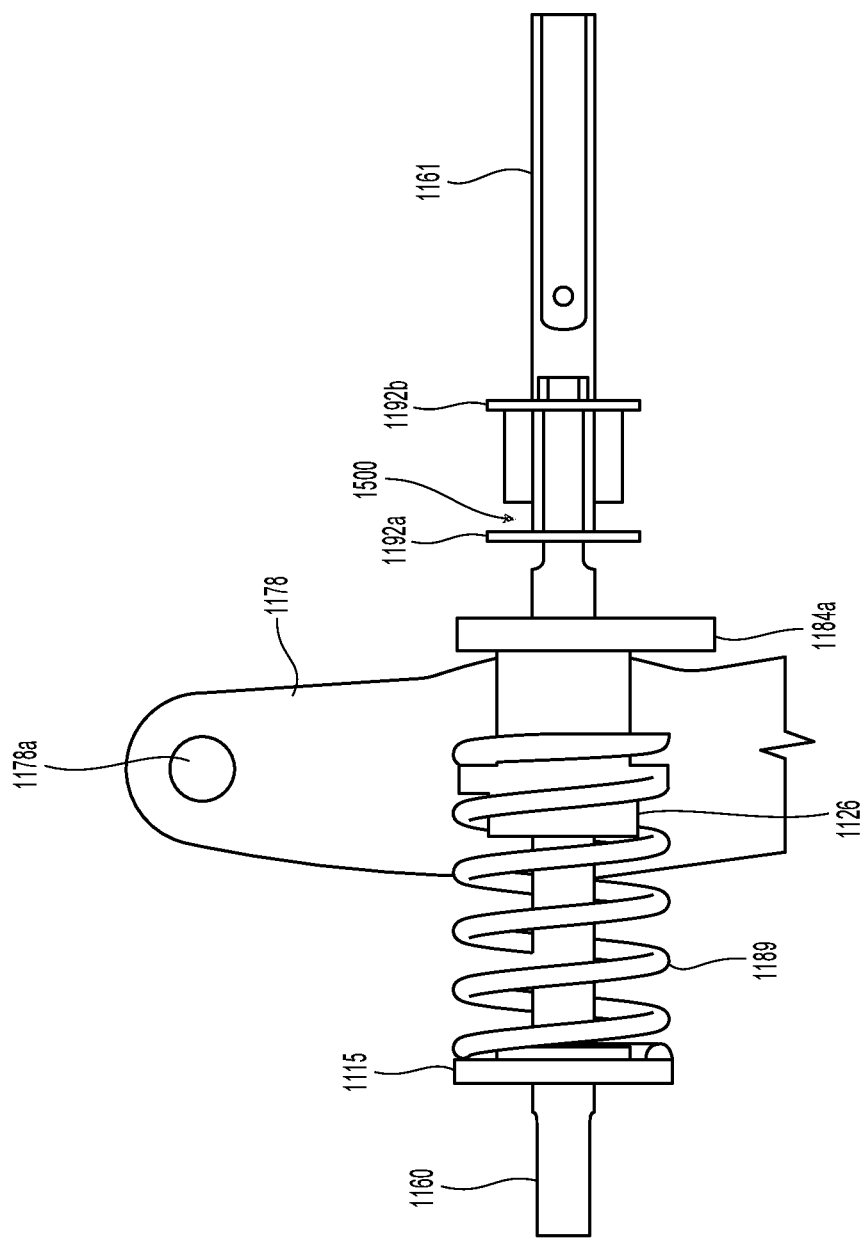
FIG. 14D is an enlarged, partial phantom view of a drive assembly of the electrosurgical forceps of FIG. 14A shown in an initial position.

As best shown in FIG. 14D, rear drive tube 1160 supports a rear washer 1192a that is configured to operably couple to a front drive tube 1161. A front washer 1192b is supported atop front drive tube 1161 and operably couples to rear drive tube 1160 at a distal end thereof. A stopper tube 1193 mounts atop the front drive tube 1161 between the front and rear washers 1192b, 1192a and is configured to slide atop the front drive tube 1161 upon actuation of the movable handle 1122 as explained in more detail below. A spring 1119 biases the stopper tube 1193 in a distal-most orientation.

When the movable handle 1122 is unactuated or open, a dead space area 1500 is exposed between the proximal end of the stopper tube 1193 and the rear washer 1192a. As explained in more detail below, as the movable handle 1122 moves through its range of motion from open to fully actuated, the exposed dead space area 1500 is eliminated prior to offloading the closure force to the jaw force spring 1189 and eventually enable in-line activation of the forceps 1000. This additional range of motion of the handle 1122 through the dead space 1500 provides the surgeon with a better tactile feel prior to compression of tissue and activation of energy.

Figure 15A:
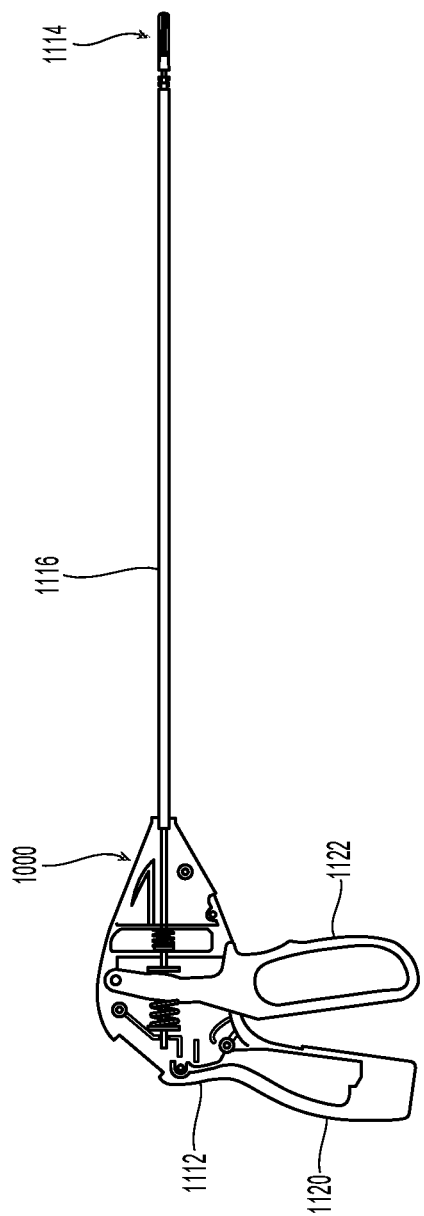
FIG. 15A is an internal, side view of the electrosurgical forceps of FIG. 14A with jaw members of the end effector assembly shown in a closed configuration and the movable handle partially actuated with a stopper tube shown in a distal-most configuration and the jaw force spring shown in an unbiased configuration.
Figure 15B:
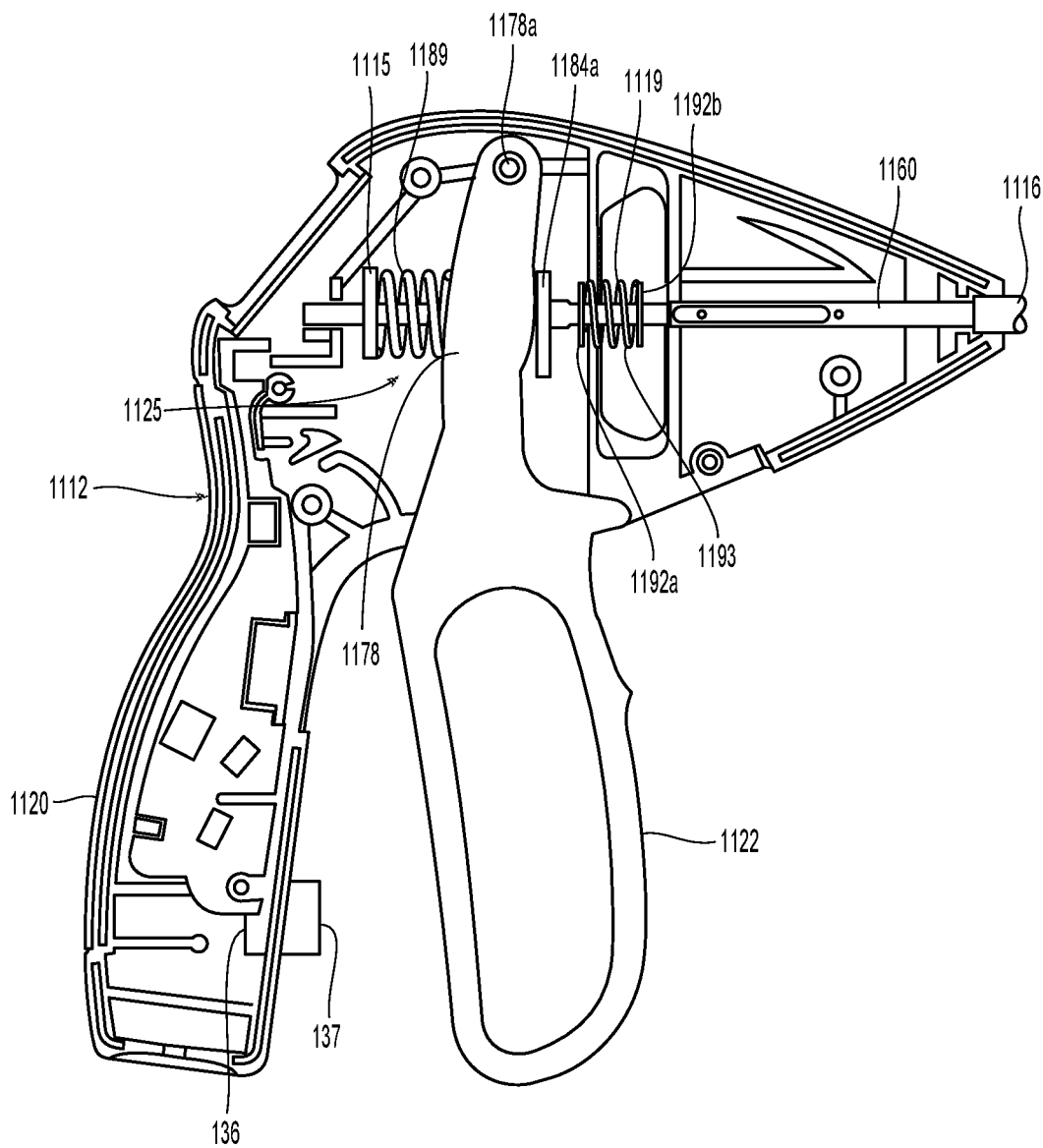
FIG. 15B is an enlarged view of the electrosurgical forceps of FIG. 15A.
Figure 15C:
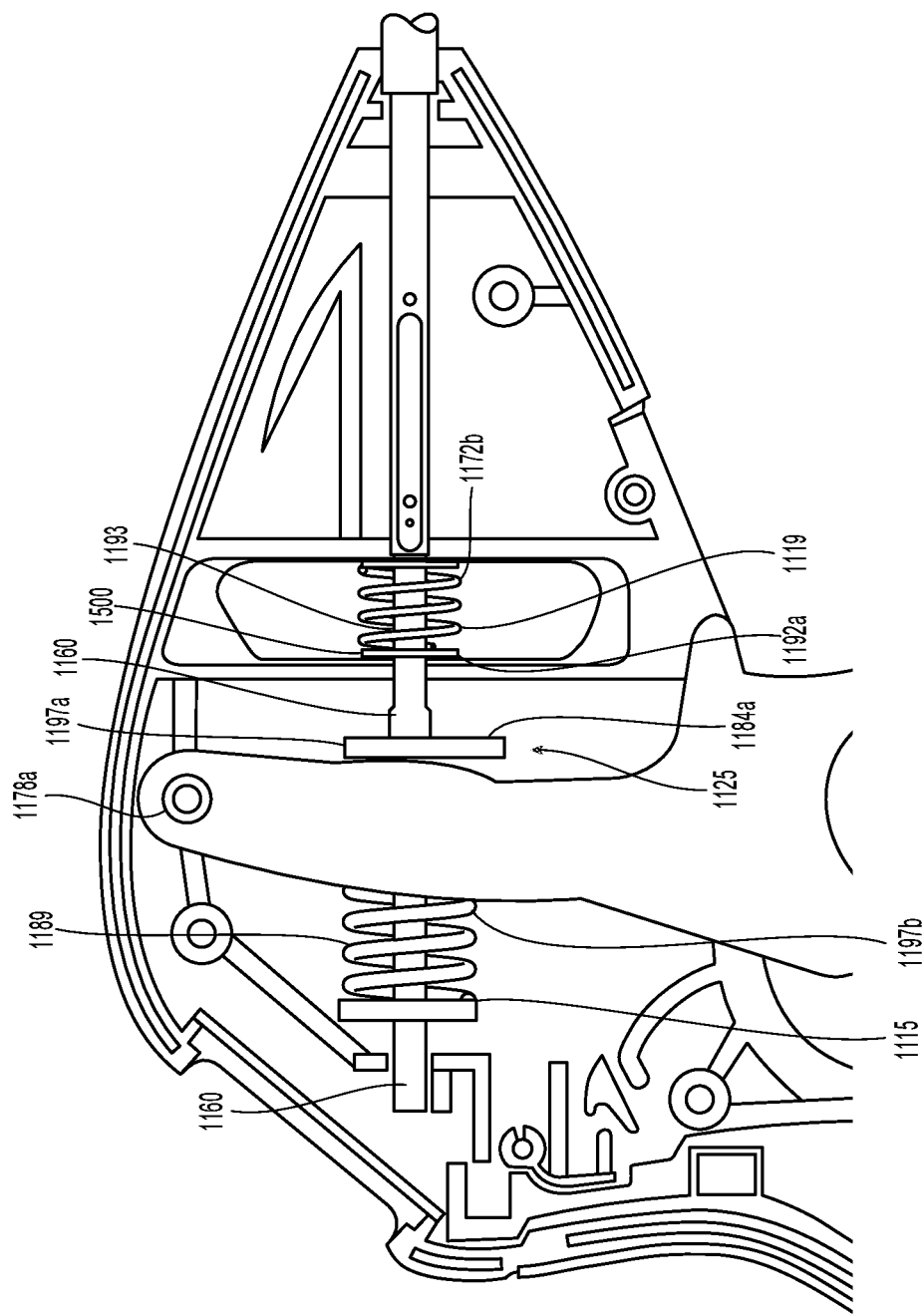
FIG. 15C is a greatly-enlarged view of the electrosurgical forceps of FIG. 15A illustrating a dead space between the stopper tube and a rear washer disposed on a rear drive tube of the elongated shaft.
Figure 15D:
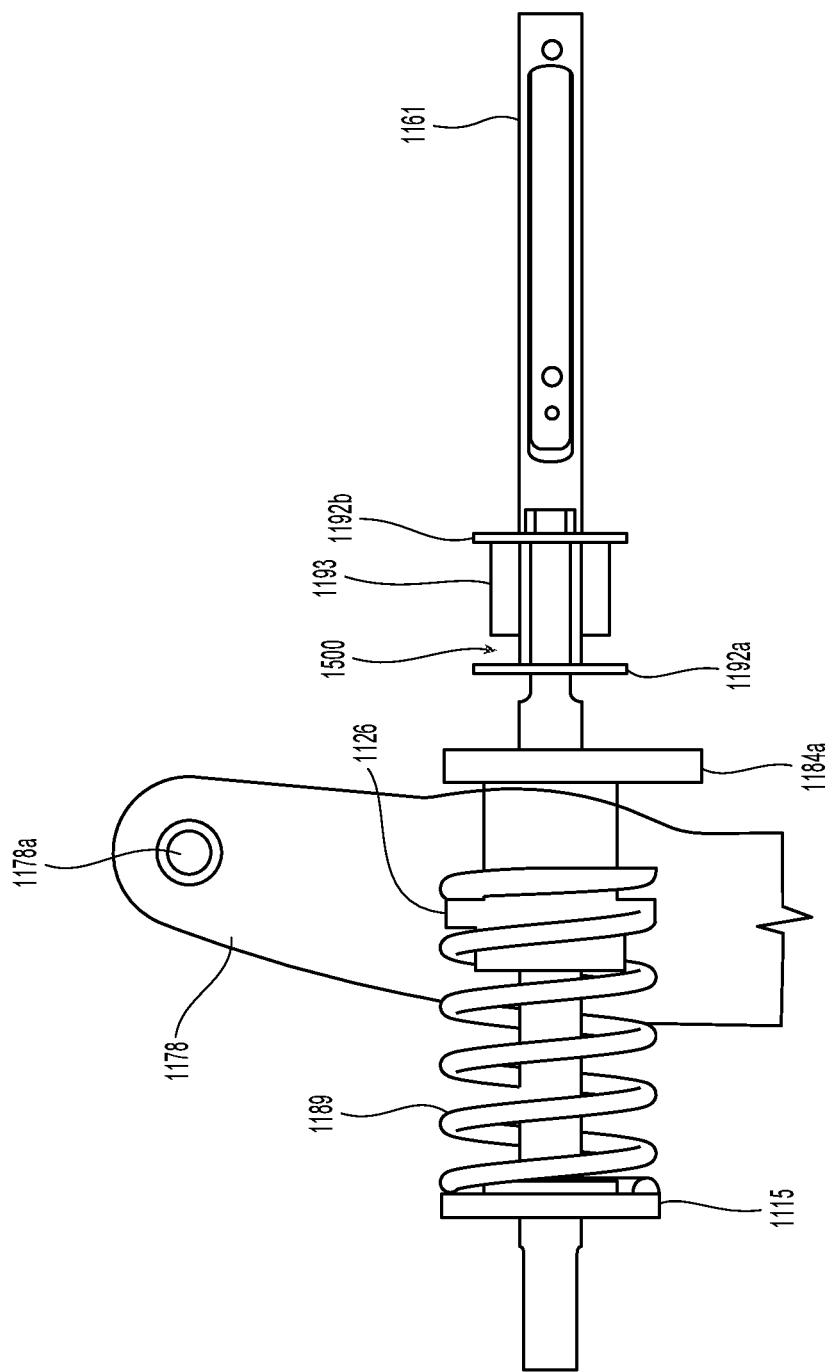
FIG. 15D is an enlarged, partial phantom view of the drive assembly of the electrosurgical forceps of FIG. 14A shown with the movable handle in a further actuated position to effect closure of the jaw members of the end effector assembly.
Figure 16A:
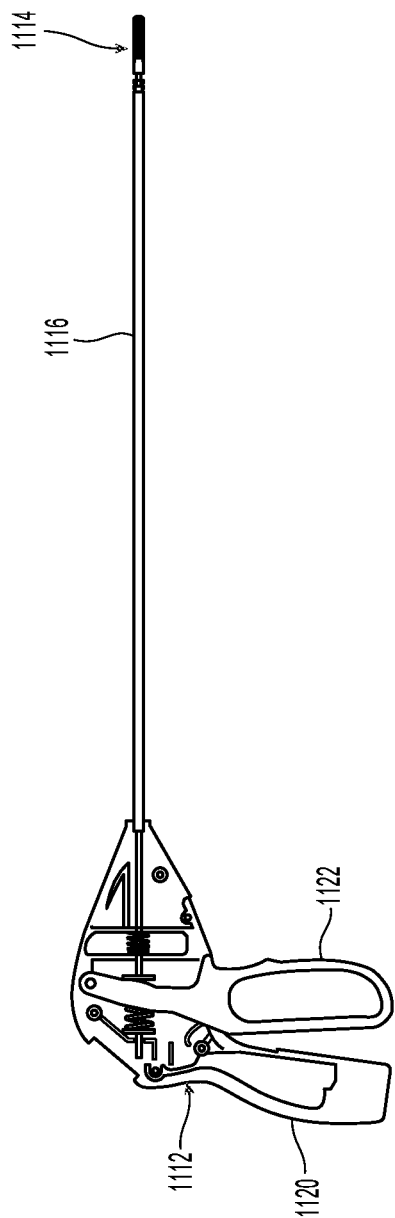
FIG. 16A is an internal, side view of the electrosurgical forceps of FIG. 14A with the end effector assembly shown in the closed configuration and the movable handle further actuated to eliminate the dead space between the stopper tube and the rear washer while the jaw force spring remains in an unbiased configuration.
Figure 16B:
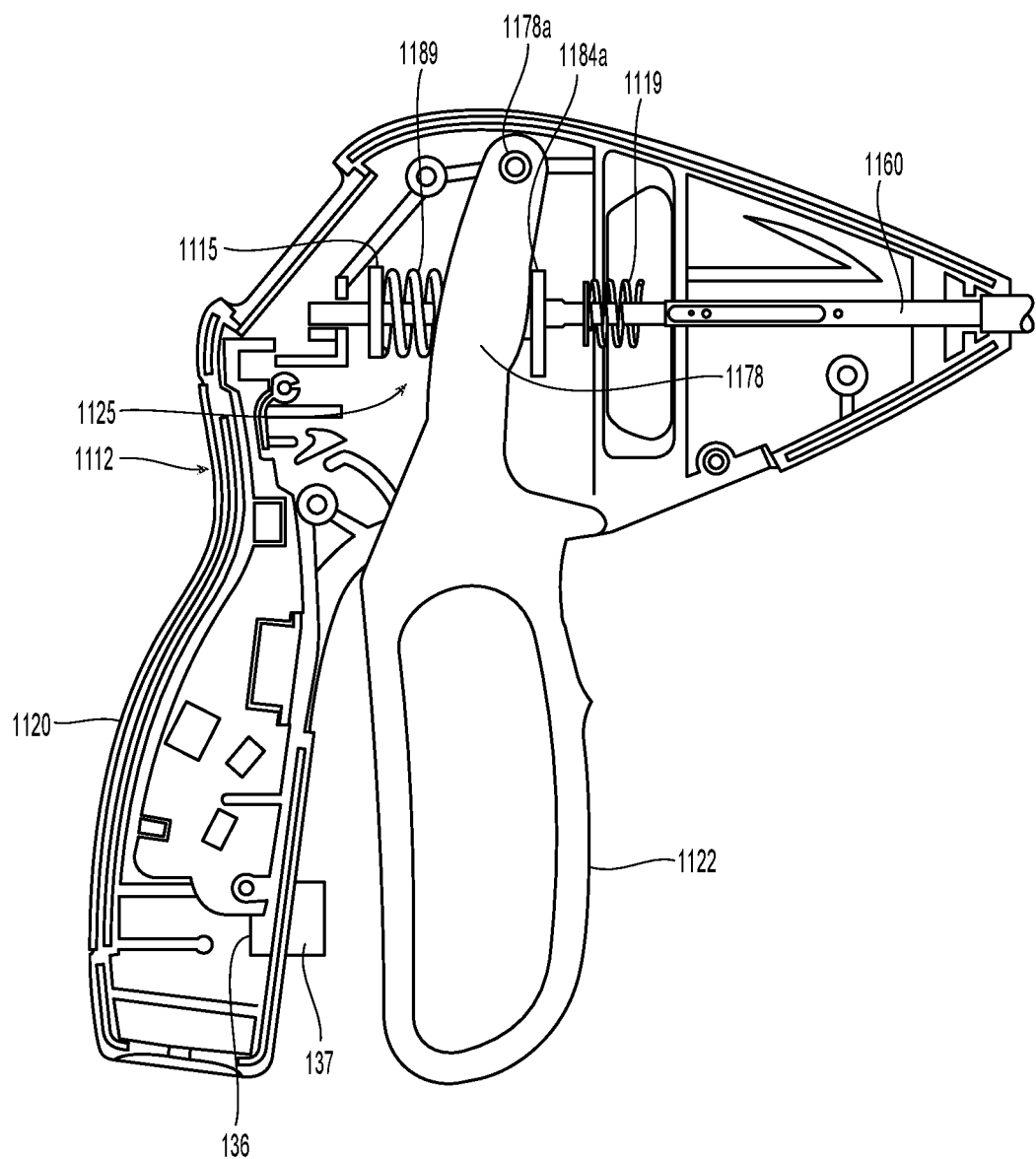
FIG. 16B is an enlarged view of the electrosurgical forceps of FIG. 16A.
Figure 16C:
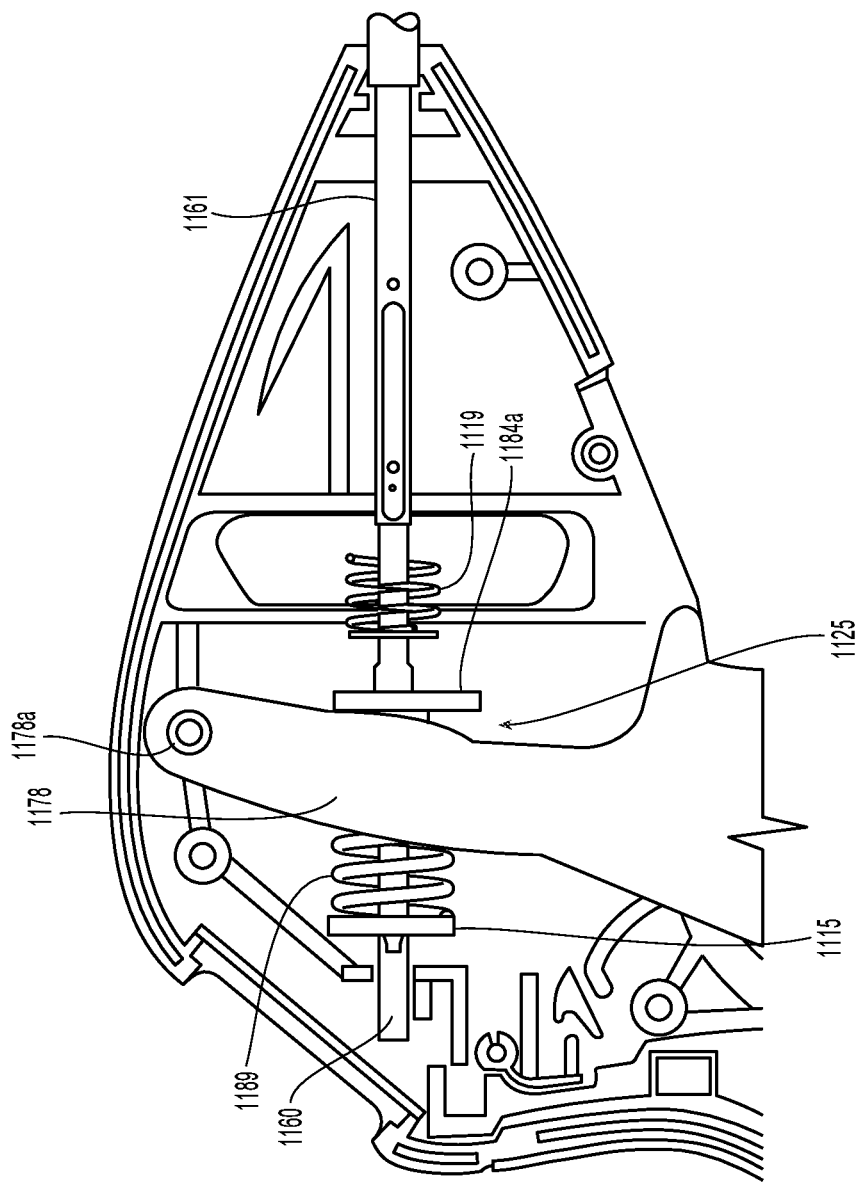
FIG. 16C is a greatly-enlarged view of the electrosurgical forceps of FIG. 16A illustrating the elimination of the dead space between the stopper tube and the rear washer.
Figure 16D:
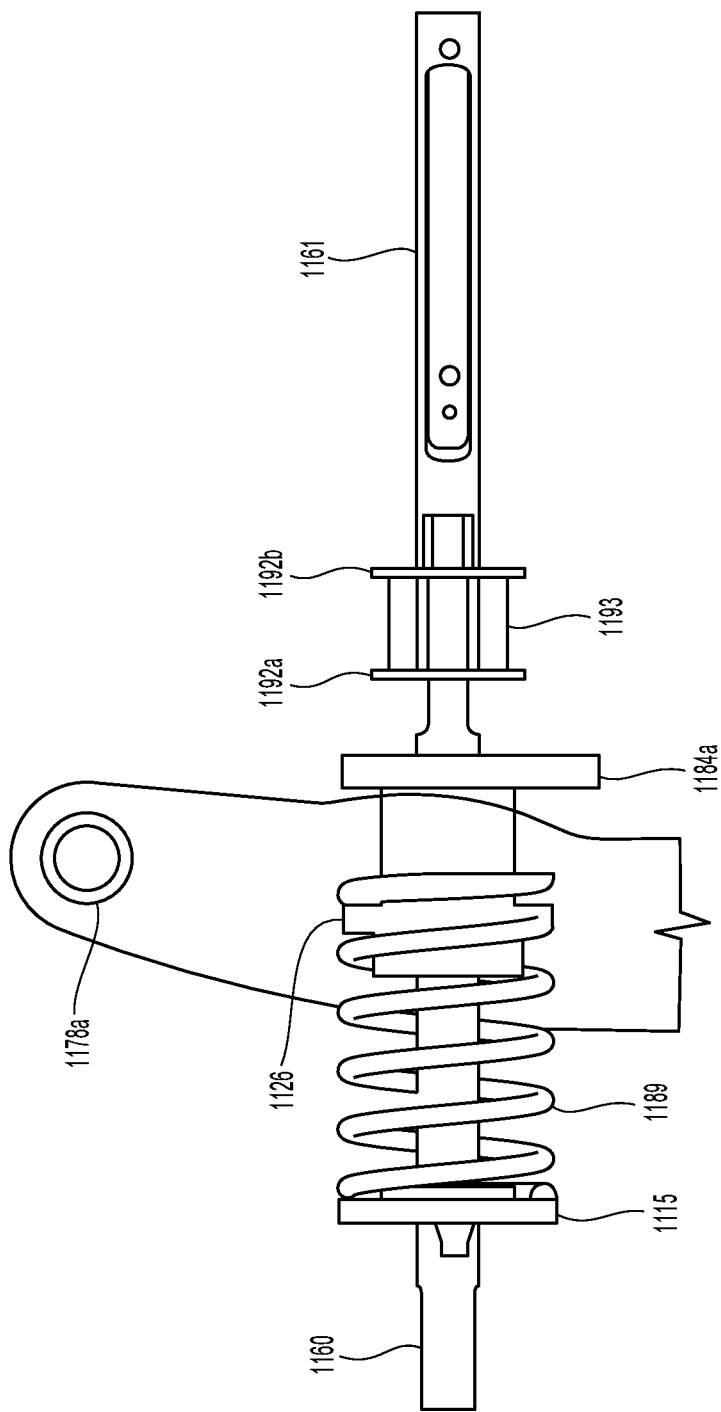
FIG. 16D is an enlarged, partial phantom view of the drive assembly of the electrosurgical forceps of FIG. 14A shown in a further actuated position which effectively eliminates the dead space during the range of motion and prior to applying a closure force to the jaw members of the end effector assembly.
Figure 17A:
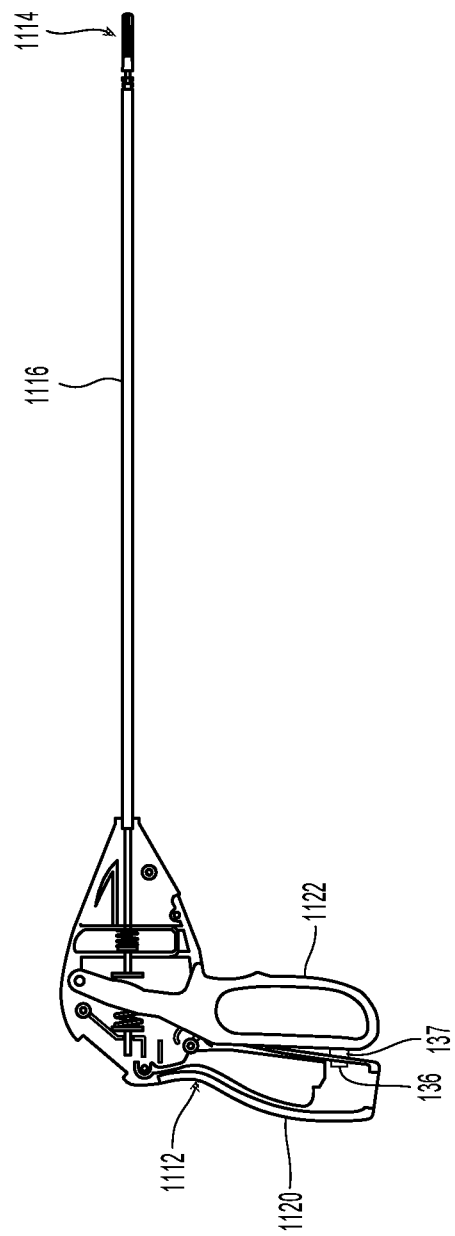
FIG. 17A is an internal, side view of the electrosurgical forceps of FIG. 14A with the end effector assembly shown in the closed configuration and the movable handle fully actuated to initiate electrosurgical energy with the jaw force spring spring shown in a biased configuration.
Figure 17B:
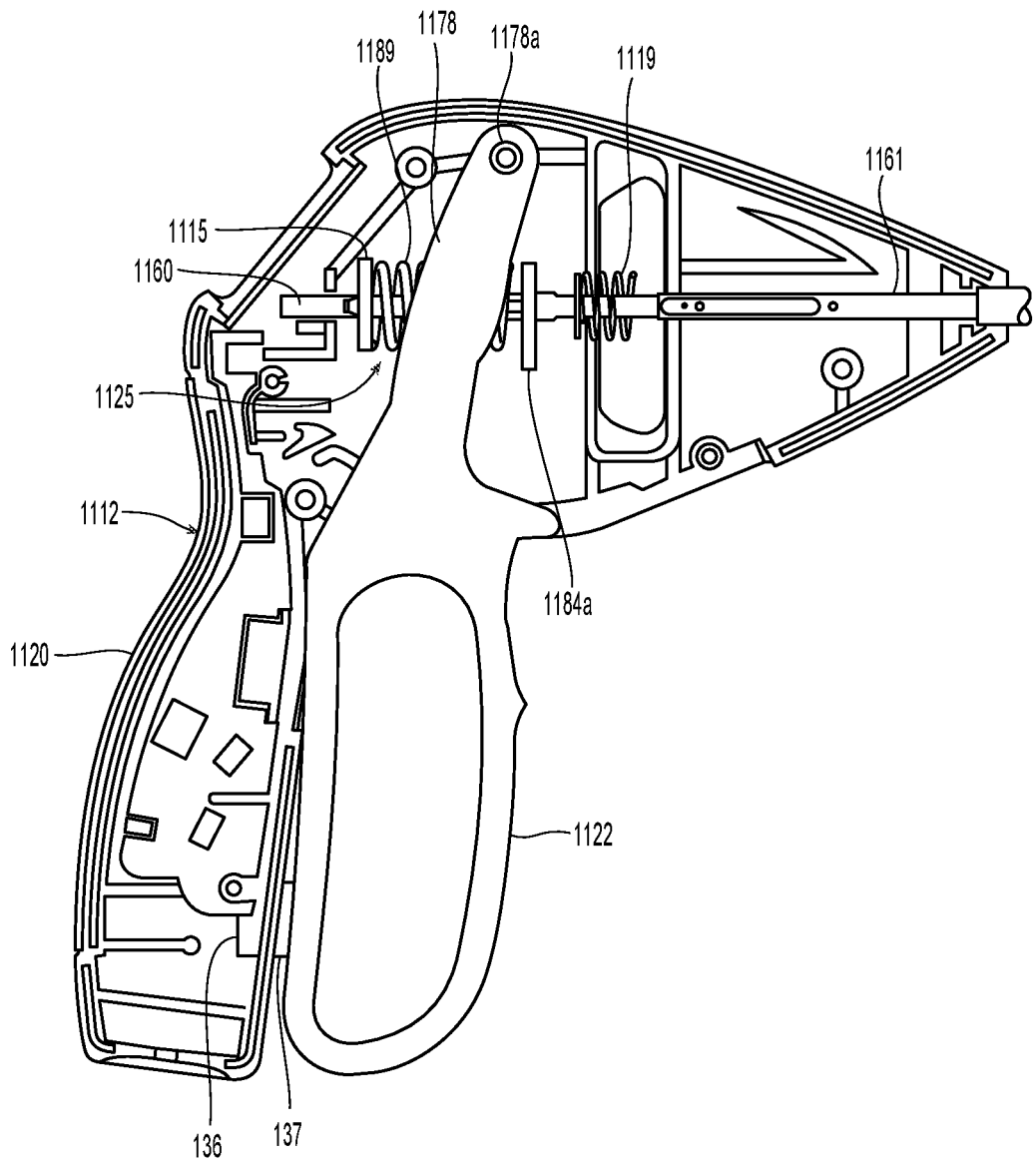
FIG. 17B is an enlarged view of the electrosurgical forceps of FIG. 17A.
Figure 17C:
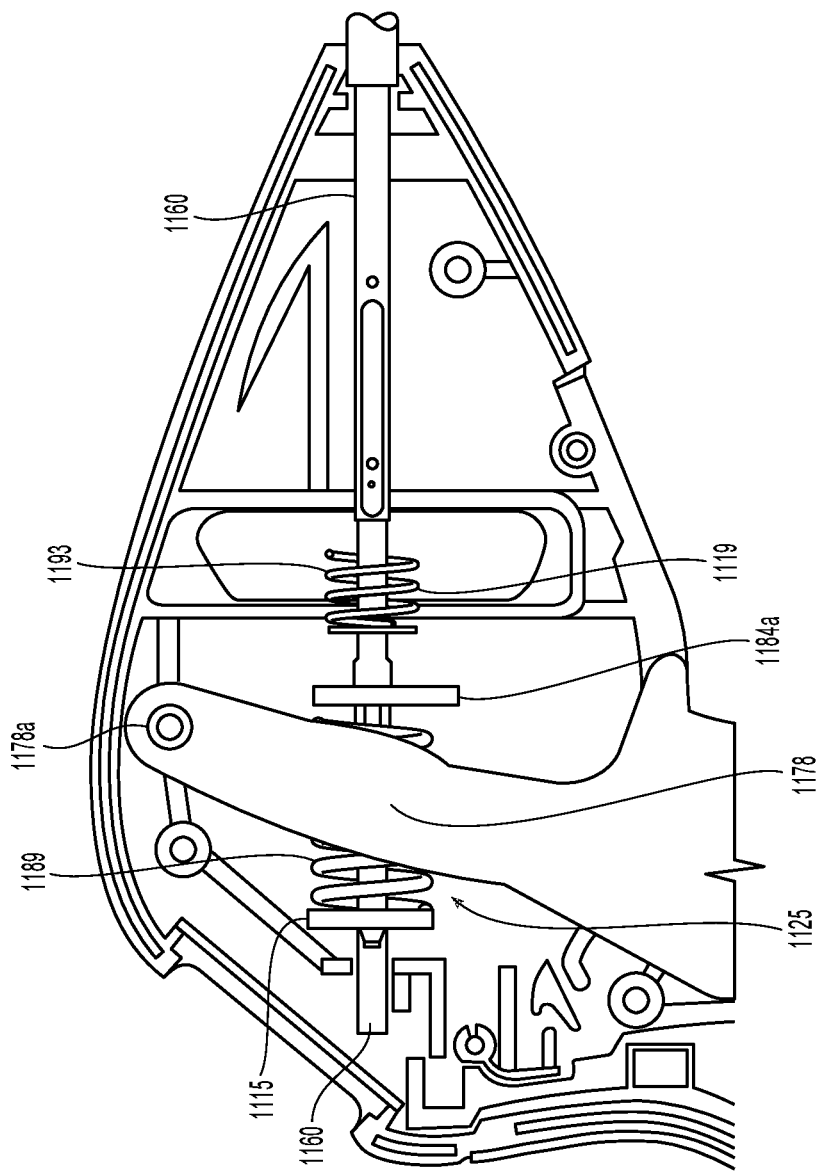
FIG. 17C is a greatly-enlarged view of the electrosurgical forceps of FIG. 17A illustrating the biasing of the jaw force spring to apply pressure to tissue disposed between jaw members of the end effector assembly.
Figure 17D:
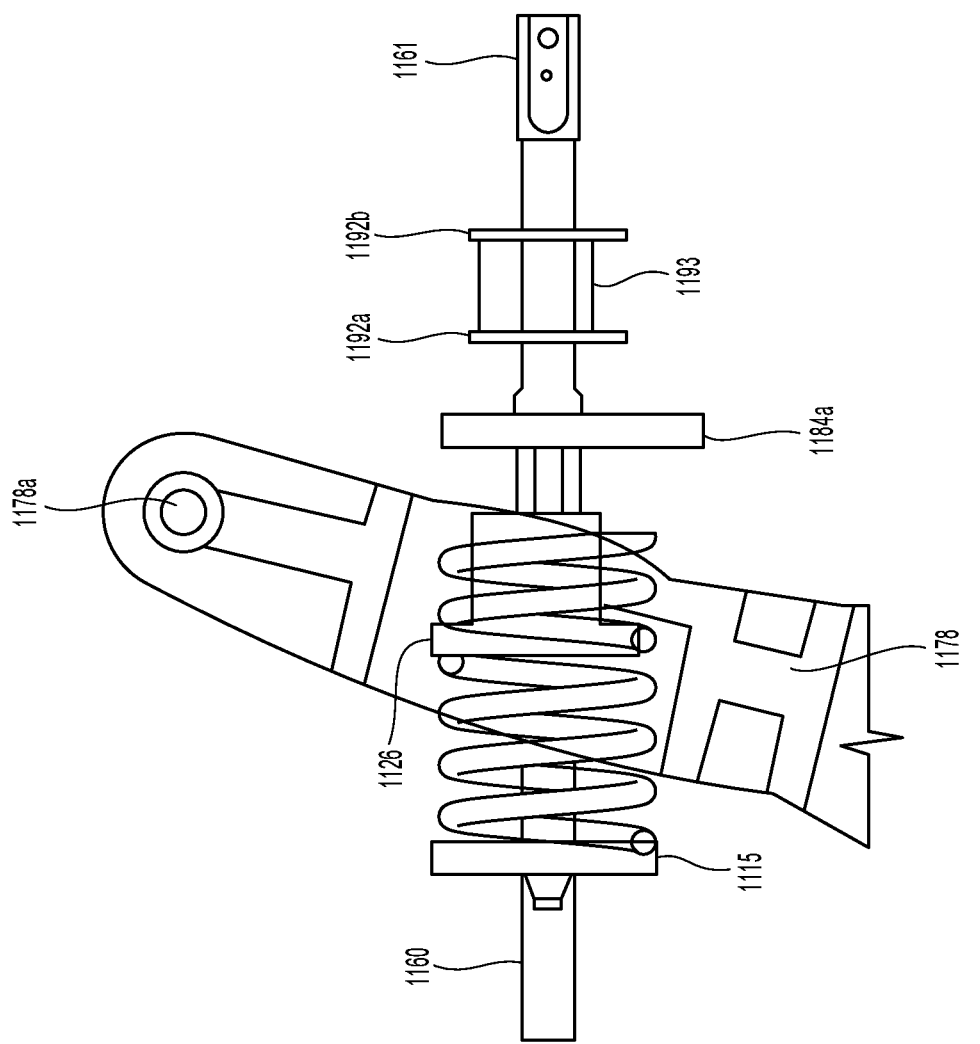
FIG. 17D is an enlarged, partial phantom view of the drive assembly of the electrosurgical forceps of FIG. 14A shown in the fully actuated position applying a closure force to the jaw members of the end effector assembly.

As best shown in FIGS. 15A-15D, when movable handle 1122 is initially actuated, clevis 1178 is rotated such that front drive surface 1197a biases against distal spring washer 1184a and rear tube and front tube 1160, 1161 move proximally causing the jaw members 1130, 1132 to move to the closed position (See comparison of FIGS. 14D and 15D). Notably, in this initial position, the dead space area 1500 is maintained between the proximal end of stopper tube 1193 and the rear washer 1192a. Moreover, since spring collar 1126 remains stationary during this initial movement of movable handle 1122, the jaw force spring 1189 remains uncompressed.

Turning now to FIGS. 16A-16D, continued movement of handle 1122 proximally causes rear drive tube 1160 to move proximally pulling front washer 1192b proximally relative to rear washer 1192a along with stopper tube 1193 and against the spring 1119. Ultimately, the stopper tube 1193 bottoms out against the rear washer 1192a thereby eliminating the dead space 1500 between the stopper tube 1193 and the rear washer 1192a. As mentioned above, the additional range of motion of the handle 1122 through the dead space 1500 provides the surgeon with a better tactile feel prior to compression of tissue and activation of energy.

As best shown in FIGS. 17A-17D, once the dead space 1500 has been eliminated, continued movement of the movable handle 1122 causes the clevis 1178 to move the spring collar 1126 proximally against the jaw force spring 1189 along the rear tube 1160 while the front and rear drive tubes 1160, 1161 remain stationary. The jaw force spring 1189 provides the necessary closure force to jaw members 1130, 1132 to enable the forceps 1000 to seal tissue upon application of electrical energy, e.g., when the movable handle 1122 activates the delivery of electrical energy upon engagement of activation button 137 when fully actuated. The closure force may be within a range of about 3 kg/cm$^2$ to about 15 kg/cm$^2$. As can be appreciated, providing the dead space 1500 can reduce the chances of unintended activation.

Upon release of the movable handle 1122 relative to stationary handle 1120, the following happens in sequence as the movable handle 1122 is released distally: the delivery of energy is terminated when movable handle 1122 disengages activation button 137; the bias of jaw force spring 1189 forces spring collar 1126 distally until the spring collar 1126 bottoms out against distal spring washer 1184a; the bias of spring 1119 forces stopper tube 1193 distally along with rear tube 1160 and front washer 1192b to reconstitute the dead space 1500 therebetween; and, upon full release, the movable handle 1122 moves both rear drive tube and front drive tube 1160, 1161 distally to open the jaw members 1130, 1132 and release the sealed tissue therebetween.

The present disclosure also relates to a method for sealing tissue using a forceps 1000 and includes: actuating the handle 1122 towards the housing 1112 of the forceps 1000 to move the front and rear drive tubes 1161, 1160 to close the first jaw member 1130 and the second jaw member 1132 to grasp tissue; further actuating the handle 1122 beyond the initial movement of the handle 1122 in the same direction to move the rear drive tube 1160 relative to the front drive tube 1161 and pull the front washer 1192b proximally forcing the stopper tube 1193 to slide proximally towards the rear washer 1192a to eliminate the dead space 1500 between the rear washer 1192a and the stopper tube 1193; and further actuating the handle 1122 towards the housing 1112 to compress the jaw force spring 1189 and move the spring collar 1126 disposed atop the rear drive tube 1160 to provide a closure force between the first and second jaw members 1130, 1132.

The method may additionally include further actuating the handle 1122 towards the housing 1112 to activate the switch 136 disposed in the housing 1112 to provide electrosurgical energy to the jaw members 1130, 1132 to seal tissue disposed therebetween. The closure force may be within a range of about 3 kg/cm$^2$ to about 15 kg/cm$^2$. The method may additionally include: further actuating the handle 1122 towards the housing 1112 to engage an activation button 137 disposed in angular registration with the handle 1122, the activation button 137 generating a response to engagement with the handle 1122; and further actuating the handle 1122 to depress the activation button 137 to activate the switch 136 to provide electrosurgical energy to the jaw members 1130, 1132 to seal tissue disposed therebetween. The response may be tactile and/or audible.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto. For example, the above-described forceps is commonly referred to as having a pull-to-close actuation arrangement, the same concepts discussed herein are contemplated to work with a forceps having a push-to-close actuation arrangement. Certain features may have to be slightly re-arranged to cover this alternative, e.g., the washer and dead space would arrangement be opposite. Moreover, the various advantages and concepts discussed herein relating to the dead space arrangement may be utilized with other actuation mechanisms (or activation mechanisms), e.g., the switch 136.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a housing;
   an elongated shaft extending distally from the housing and configured to support an end effector assembly at a distal end thereof, the end effector assembly including first and second jaw members; and
   an actuator operably coupled to a drive assembly disposed within the housing to actuate the end effector assembly and move at least one of the first or second jaw members relative to the other jaw member to grasp tissue therebetween, the drive assembly including:
      a rear drive tube and a front drive tube, the rear drive tube including a front washer disposed at a distal end thereof, the front drive tube including a rear washer disposed at a proximal end thereof, the front and rear washers urged apart via a biasing member disposed therebetween to define a dead space therebetween;
   wherein initial actuation of the actuator moves the front and rear drive tubes together with one another to move the at least one jaw member to grasp tissue and, once the first and second jaw members are closed, further movement of the actuator in the same direction moves the rear drive tube relative to the front drive tube to move the front washer towards the rear washer to eliminate the dead space.

2. The surgical instrument according to claim 1, wherein the actuator is configured to move proximally from a distal-most position to move the at least one of the first or second jaw members.

3. The surgical instrument according to claim 1, wherein initial movement of the actuator moves the front and rear drive tubes proximally.

4. The surgical instrument according to claim 1, wherein further movement of the actuator beyond the initial actuation of the actuator moves the front washer proximally relative to the rear washer and against the bias of the biasing member to eliminate the dead space therebetween.

5. The surgical instrument according to claim 1, wherein, after movement of the actuator to eliminate the dead space, further movement of the actuator compresses a second biasing member disposed between a drive spring washer and a rear stop to provide a closure force between the first and second jaw members.

6. The surgical instrument according to claim 5, wherein the closure force is within a range of about 3 kg/cm$^2$ to about 15 kg/cm$^2$.

7. The surgical instrument according to claim 5, wherein the actuator initially compresses the second biasing member to provide the closure force between the first and second jaw members, and wherein further movement of the actuator actuates a switch disposed in the housing to provide electrosurgical energy to the first or second jaw members to seal tissue disposed therebetween.

8. The surgical instrument according to claim 7, wherein the switch is operably associated with an activation button and is disposed in angular registration with the actuator such that proximal movement of the actuator towards a fully actuated position operably engages the activation button to activate the switch.

9. The surgical instrument according to claim 8, wherein the activation button is configured to engage a mechanical interface disposed within the housing, the mechanical interface configured to generate a response to engagement with the activation button.

10. The surgical instrument according to claim 9, wherein the response is at least one of tactile and audible.

11. A surgical instrument, comprising:
a housing;
an elongated shaft extending distally from the housing and configured to support an end effector assembly at a distal end thereof, the end effector assembly including first and second jaw members; and
a drive assembly configured to actuate the end effector assembly and move at least one of the first or second jaw members relative to the other jaw member to grasp tissue therebetween, the drive assembly including:
a rear drive tube and a front drive tube, the rear drive tube including a front washer disposed at a distal end thereof, the front drive tube including a rear washer disposed at a proximal end thereof, wherein the front and rear washers are urged apart via a spring disposed therebetween to define a dead space therebetween;
wherein initial actuation of the drive assembly moves the front and rear drive tubes together with one another to move the at least one of the first or second jaw members to grasp tissue and, once the first and second jaw members are closed, further actuation of the drive assembly in the same direction moves the rear drive tube relative to the front drive tube to move the front washer towards the rear washer to eliminate the dead space.

12. The surgical instrument according to claim 11, wherein the drive assembly is actuated by a handle configured to move proximally from a distal-most position towards the housing to move the first and second jaw members.

13. The surgical instrument according to claim 12, wherein initial movement of the handle moves the front and rear drive tubes proximally.

14. The surgical instrument according to claim 13, wherein further movement of the handle moves the front washer proximally towards the rear washer to eliminate the dead space therebetween.

15. The surgical instrument according to claim 11, wherein, after eliminating the dead space, further actuation of the drive assembly compresses a jaw force spring to provide a closure force between the first and second jaw members.

16. The surgical instrument according to claim 15, wherein the closure force is within a range of about 3 kg/cm$^2$ to about 15 kg/cm$^2$.

17. The surgical instrument according to claim 15, wherein the further actuation initially compresses the jaw force spring to provide the closure force to the first and second jaw members, and wherein further actuation actuates a switch disposed in the housing to provide electrosurgical energy to the first and second jaw members to seal tissue disposed therebetween.

18. The surgical instrument according to claim 17, wherein the switch is operably associated with an activation button and is disposed in angular registration with and actuator such that proximal movement of the actuator towards a fully actuated position operably engages the activation button to activate the switch.

19. The surgical instrument according to claim 18, wherein the activation button is configured to engage a mechanical interface disposed within the housing, the mechanical interface configured to generate a response to engagement with the activation button.

20. The surgical instrument according to claim 19, wherein the response is at least one of tactile and audible.

* * * * *